United States Patent
Leblanc et al.

(10) Patent No.: US 7,582,633 B2
(45) Date of Patent: Sep. 1, 2009

(54) AZACYCLOALKANE DERIVATIVES AS INHIBITORS OF STEAROYL-COENZYME A DELTA-9 DESATURASE

(75) Inventors: Yves Leblanc, Kirkland (CA); David Powell, Verdun (CA); Yeeman K. Ramtohul, Pierrefonds (CA); Serge Léger, Notre-Dame-de-l'ile-Perrot (CA)

(73) Assignee: Merck Frosst Canada L.L.C., Kirkland, Quebec (CA)

(*) Notice: Subject to any disclaimer, the term of this patent is extended or adjusted under 35 U.S.C. 154(b) by 0 days.

(21) Appl. No.: 12/011,309

(22) Filed: Jan. 25, 2008

(65) Prior Publication Data
US 2008/0182838 A1 Jul. 31, 2008

Related U.S. Application Data

(60) Provisional application No. 60/897,675, filed on Jan. 26, 2007.

(51) Int. Cl.
| | |
|---|---|
| *C07D 401/14* | (2006.01) |
| *C07D 403/14* | (2006.01) |
| *A61K 31/41* | (2006.01) |
| *A61K 31/415* | (2006.01) |
| *A61K 31/4164* | (2006.01) |
| *A61K 31/4192* | (2006.01) |
| *A61K 31/4196* | (2006.01) |
| *A61K 31/421* | (2006.01) |
| *A61K 31/425* | (2006.01) |
| *A61P 3/10* | (2006.01) |
| *A61P 3/04* | (2006.01) |

(52) U.S. Cl. ............ 514/252.13; 514/252.18; 544/359; 544/360

(58) Field of Classification Search ......... 544/359, 544/360; 514/252.13, 252.18
See application file for complete search history.

(56) References Cited

U.S. PATENT DOCUMENTS

| 2005/0119251 A1 | 6/2005 | Fu et al. |
| 2005/0234033 A1 | 10/2005 | Anandan et al. |
| 2008/0132542 A1 | 6/2008 | Lachance et al. |

FOREIGN PATENT DOCUMENTS

| CA | 2 533 897 | 2/2005 |
| WO | WO 97/26258 | 7/1997 |
| WO | WO 2006/034279 A1 | 3/2006 |
| WO | WO 2006/034312 A1 | 3/2006 |
| WO | WO 2006/034315 A2 | 3/2006 |
| WO | WO 2006/034315 A3 | 3/2006 |
| WO | WO 2006/034338 A1 | 3/2006 |
| WO | WO 2006/034341 A2 | 3/2006 |
| WO | WO 2006/034341 A3 | 3/2006 |
| WO | WO 2006/034440 A2 | 3/2006 |
| WO | WO 2006/034440 A3 | 3/2006 |
| WO | WO 2006/034441 A1 | 3/2006 |
| WO | WO 2006/086445 A2 | 8/2006 |
| WO | WO 2006/086445 A3 | 8/2006 |
| WO | WO 2006/086447 A2 | 8/2006 |
| WO | WO 2006/086447 A3 | 8/2006 |
| WO | WO 2006/101521 A2 | 9/2006 |
| WO | WO 2006/101521 A3 | 9/2006 |
| WO | WO 2006/125181 A2 | 11/2006 |
| WO | WO 2006/125181 A3 | 11/2006 |
| WO | WO 2006/130986 A1 | 12/2006 |
| WO | WO 2007/009236 A1 | 1/2007 |
| WO | WO 2007/038865 A1 | 4/2007 |
| WO | WO 2007/056846 A1 | 5/2007 |
| WO | WO 2007/071023 A1 | 6/2007 |
| WO | WO 2007/134457 A1 | 11/2007 |
| WO | WO 2007/143823 A1 | 12/2007 |
| WO | WO 2007/143824 A1 | 12/2007 |
| WO | WO 2008/017161 A1 | 2/2008 |
| WO | WO 2008/046226 A1 | 4/2008 |
| WO | WO 2008/064474 A1 | 6/2008 |

OTHER PUBLICATIONS

Cecil Textbook of Medicine, edited by Bennet, J.C., and Plum F., 20th edition, vol. 1, 1004-1010, 1996.*
Freshney et al., Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Dobrzyn et al., Journal of Phisiology and Pharmacology, 57, Suppl. 10, 31-42, 2006.*
Flowers et al., Current Opinion in Lipidology, 19, 248-256, 2008.*
Liu, G. et al., "Discovery of Potent, Selective, Orally Bioavailable Stearoyl-CoA Desaturase 1 Inhibitors", J. Med. Chem., vol. 50, pp. 3086-3100, 2007.
Zhao, H. et al., "Discovery of 1-(4-phenoxypiperidin-1-yl)-2-arylaminoethanone stearoyl-CoA desaturase 1 inhibitors", Bioorganic & Medicinal Chemistry Letters, vol. 17, pp. 3388-3391, 2007.

* cited by examiner

*Primary Examiner*—Venkataraman Balasubramanian
(74) *Attorney, Agent, or Firm*—Philippe L. Durette; Catherine D. Fitch

(57) ABSTRACT

Azacycloalkane derivatives of structural formula I are selective inhibitors of stearoyl-coenzyme A delta-9 desaturase (SCD1) relative to other known stearoyl-coenzyme A desaturases. The compounds of the present invention are useful for the prevention and treatment of conditions related to abnormal lipid synthesis and metabolism, including cardiovascular disease, such as atherosclerosis; obesity; diabetes; neurological disease; metabolic syndrome; insulin resistance; and liver steatosis.

(I)

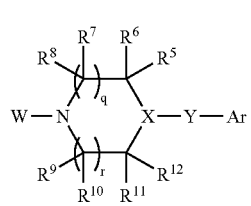

19 Claims, No Drawings

AZACYCLOALKANE DERIVATIVES AS INHIBITORS OF STEAROYL-COENZYME A DELTA-9 DESATURASE

CROSS-REFERENCE TO RELATED APPLICATIONS

The present invention is related to U.S. provisional application Ser. No. 60/897,675, filed Jan. 26, 2007, the contents of each of which are hereby incorporated by reference.

FIELD OF THE INVENTION

The present invention relates to azacycloalkane derivatives which are inhibitors of stearoyl-coenzyme A delta-9 desaturase (SCD) and the use of such compounds to control, prevent and/or treat conditions or diseases mediated by SCD activity. The compounds of the present invention are useful for the control, prevention and treatment of conditions and diseases related to abnormal lipid synthesis and metabolism, including cardiovascular disease, such as atherosclerosis; obesity; diabetes; neurological disease; metabolic syndrome; insulin resistance; cancer; and hepatic steatosis.

BACKGROUND OF THE INVENTION

At least three classes of fatty acyl-coenzyme A (CoA) desaturases (delta-5, delta-6 and delta-9 desaturases) are responsible for the formation of double bonds in mono- and polyunsaturated fatty acyl-CoAs derived from either dietary sources or de novo synthesis in mammals. The delta-9 specific stearoyl-CoA desaturases (SCDs) catalyze the rate-limiting formation of the cis-double bond at the C9-C10 position in monounsaturated fatty acyl-CoAs. The preferred substrates are stearoyl-CoA and palmitoyl-CoA, with the resulting oleoyl and palmitoleoyl-CoA as the main components in the biosynthesis of phospholipids, triglycerides, cholesterol esters and wax esters (Dobrzyn and Natami, *Obesity Reviews*, 6: 169-174 (2005)).

The rat liver microsomal SCD protein was first isolated and characterized in 1974 (Strittmatter et al., *PNAS*, 71: 4565-4569 (1974)). A number of mammalian SCD genes have since been cloned and studied from various species. For example, two genes have been identified from rat (SCD1 and SCD2, Thiede et al., *J. Biol. Chem.*, 261, 13230-13235 (1986)), Mihara, K., *J. Biochem.* (Tokyo), 108: 1022-1029 (1990)); four genes from mouse (SCD1, SCD2, SCD3 and SCD4) (Miyazaki et al., *J. Biol. Chem.*, 278: 33904-33911 (2003)); and two genes from human (SCD1 and ACOD4 (SCD2)), (Zhang, et al., *Biochem. J.*, 340: 255-264 (1991); Beiraghi, et al., *Gene*, 309: 11-21 (2003); Zhang et al., *Biochem. J.*, 388: 135-142 (2005)). The involvement of SCDs in fatty acid metabolism has been known in rats and mice since the 1970's (Oshino, N., *Arch. Biochem. Biophys.*, 149: 378-387 (1972)). This has been further supported by the biological studies of a) Asebia mice that carry the natural mutation in the SCD1 gene (Zheng et al., *Nature Genetics*, 23: 268-270 (1999)), b) SCD1-null mice from targeted gene deletion (Ntambi, et al., *PNAS*, 99: 11482-11486 (2002), and c) the suppression of SCD1 expression during leptin-induced weight loss (Cohen et al., *Science*, 297: 240-243 (2002)). The potential benefits of pharmacological inhibition of SCD activity has been demonstrated with anti-sense oligonucleotide inhibitors (ASO) in mice (Jiang, et al., *J. Clin. Invest.*, 115: 1030-1038 (2005)). ASO inhibition of SCD activity reduced fatty acid synthesis and increased fatty acid oxidation in primary mouse hepatocytes. Treatment of mice with SCD-ASOs resulted in the prevention of diet-induced obesity, reduced body adiposity, hepatomegaly, steatosis, postprandial plasma insulin and glucose levels, reduced de novo fatty acid synthesis, decreased the expression of lipogenic genes, and increased the expression of genes promoting energy expenditure in liver and adipose tissues. Thus, SCD inhibition represents a novel therapeutic strategy in the treatment of obesity and related metabolic disorders.

There is compelling evidence to support that elevated SCD activity in humans is directly implicated in several common disease processes. For example, there is an elevated hepatic lipogenesis to triglyceride secretion in non-alcoholic fatty liver disease patients (Diraison, et al., *Diabetes Metabolism*, 29: 478-485 (2003)); Donnelly, et al., *J. Clin. Invest.*, 115: 1343-1351 (2005)). The postprandial de novo lipogenesis is significantly elevated in obese subjects (Marques-Lopes, et al., *American Journal of Clinical Nutrition*, 73: 252-261 (2001)). There is a significant correlation between a high SCD activity and an increased cardiovascular risk profile including elevated plasma triglycerides, a high body mass index and reduced plasma HDL (Attie, et al., *J. Lipid Res.*, 43: 1899-1907 (2002)). SCD activity plays a key role in controlling the proliferation and survival of human transformed cells (Scaglia and Igal, *J. Biol. Chem.*, (2005)).

Other than the above mentioned anti-sense oligonucleotides, inhibitors of SCD activity include non-selective thia-fatty acid substrate analogs [B. Behrouzian and P. H. Buist, *Prostaplandins, Leukotrienes, and Essential Fatty Acids*, 68: 107-112 (2003)], cyclopropenoid fatty acids (Raju and Reiser, *J. Biol. Chem.*, 242: 379-384 (1967)), certain conjugated long-chain fatty acid isomers (Park, et al., *Biochim. Biophys. Acta*, 1486: 285-292 (2000)), a series of pyridazine derivatives disclosed in published international patent application publications WO 2005/011653, WO 2005/011654, WO 2005/011656, WO 2005/011656, and WO 2005/011657, all assigned to Xenon Pharmaceuticals, Inc., and a series of heterocyclic derivatives disclosed international patent application publications WO 2006/014168, WO 2006/034279, WO 2006/034312, WO 2006/034315, WO 2006/034338, WO 2006/034341, WO 2006/034440, WO 2006/034441, and WO 2006/034446, all assigned to Xenon Pharmaceuticals, Inc.

The present invention is concerned with novel azacycloalkane derivatives as inhibitors of stearoyl-CoA delta-9 desaturase which are useful in the treatment and/or prevention of various conditions and diseases mediated by SCD activity including those related, but not limited, to elevated lipid levels, as exemplified in non-alcoholic fatty liver disease, cardiovascular disease, obesity, diabetes, metabolic syndrome, and insulin resistance.

The role of stearoyl-coenzyme A desaturase in lipid metabolism has been described by M. Miyazaki and J. M. Ntambi, *Prostaglandins, Leukotrienes, and Essential Fatty Acids*, 68: 113-121 (2003). The therapeutic potential of the pharmacological manipulation of SCD activity has been described by A. Dobryzn and J. M. Ntambi, in "Stearoyl-CoA desaturase as a new drug target for obesity treatment," *Obesity Reviews*, 6: 169-174 (2005).

SUMMARY OF THE INVENTION

The present invention relates to azacycloalkane derivatives of structural formula I:

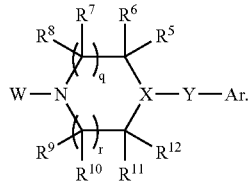

These azacycloalkane derivatives are effective as inhibitors of SCD. They are therefore useful for the treatment, control or prevention of disorders responsive to the inhibition of SCD, such as diabetes, insulin resistance, lipid disorders, obesity, atherosclerosis, and metabolic syndrome.

The present invention also relates to pharmaceutical compositions comprising the compounds of the present invention and a pharmaceutically acceptable carrier.

The present invention also relates to methods for the treatment, control, or prevention of disorders, diseases, or conditions responsive to inhibition of SCD in a subject in need thereof by administering the compounds and pharmaceutical compositions of the present invention.

The present invention also relates to methods for the treatment, control, or prevention of Type 2 diabetes, insulin resistance, obesity, lipid disorders, atherosclerosis, and metabolic syndrome by administering the compounds and pharmaceutical compositions of the present invention.

The present invention also relates to methods for the treatment, control, or prevention of obesity by administering the compounds of the present invention in combination with a therapeutically effective amount of another agent known to be useful to treat the condition.

The present invention also relates to methods for the treatment, control, or prevention of Type 2 diabetes by administering the compounds of the present invention in combination with a therapeutically effective amount of another agent known to be useful to treat the condition.

The present invention also relates to methods for the treatment, control, or prevention of atherosclerosis by administering the compounds of the present invention in combination with a therapeutically effective amount of another agent known to be useful to treat the condition.

The present invention also relates to methods for the treatment, control, or prevention of lipid disorders by administering the compounds of the present invention in combination with a therapeutically effective amount of another agent known to be useful to treat the condition.

The present invention also relates to methods for treating metabolic syndrome by administering the compounds of the present invention in combination with a therapeutically effective amount of another agent known to be useful to treat the condition.

DETAILED DESCRIPTION OF THE INVENTION

The present invention is concerned with azacycloalkane derivatives useful as inhibitors of SCD. Compounds of the present invention are described by structural formula I:

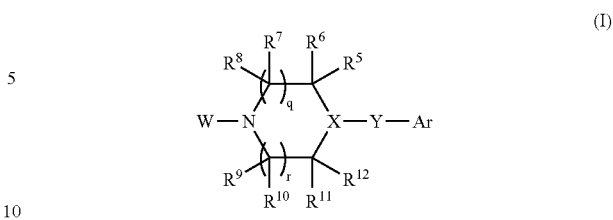

or a pharmaceutically acceptable salt thereof; wherein
each m is independently an integer from 0 to 4;
each n is independently an integer from 0 to 2;
each s is independently an integer from 1 to 3;
each t is independently an integer from 1 to 3;
q is 0 or 1;
r is 0 or 1;
Z is O, S, or $NR^4$;
X—Y is N—$CR^aR^b$, $CR^{14}$—O, $CR^{14}$—$S(O)_{0-2}$, or $CR^{13}$—$CR^aR^b$;
W is heteroaryl selected from the group consisting of:

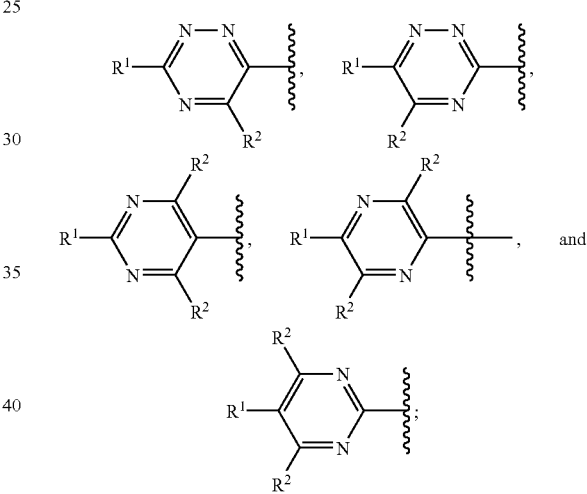

Ar is phenyl, naphthyl, or heteroaryl optionally substituted with one to five $R^3$ substituents;
$R^a$ and $R^b$ are each independently hydrogen or $C_{1-3}$ alkyl, wherein alkyl is optionally substituted with one to three substituents independently selected from fluorine and hydroxy;
$R^1$ is heteroaryl selected from the group consisting of:

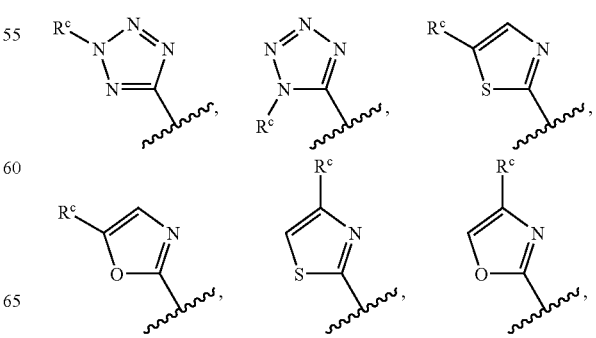

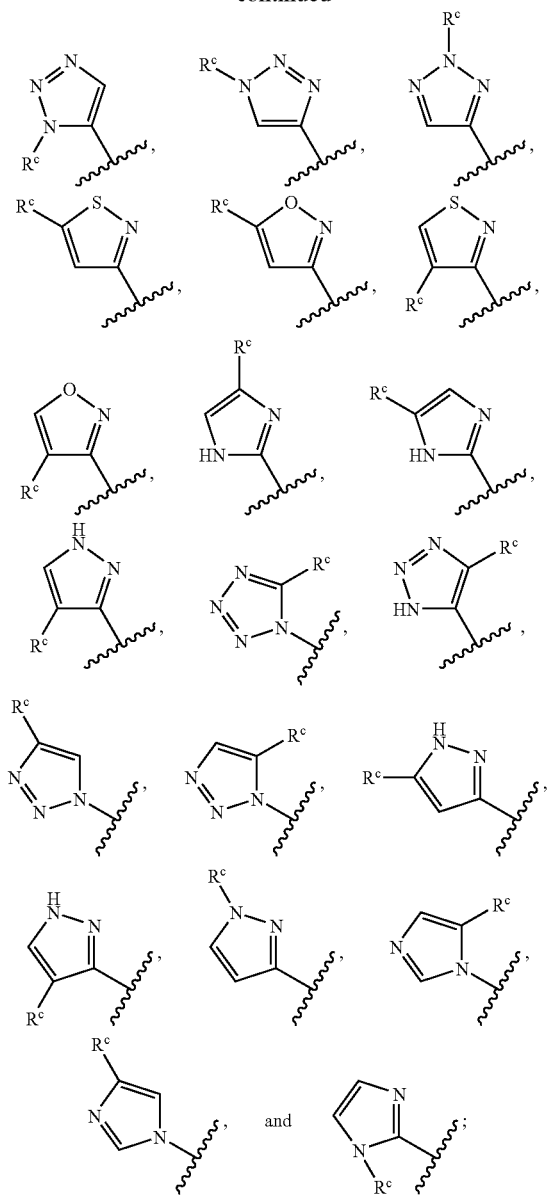

wherein $R^c$ is —$(CH_2)_mCO_2H$, —$(CH_2)_mCO_2C_{1-3}$ alkyl, —$(CH_2)_m$-Z-$(CH_2)_pCO_2H$, or —$(CH_2)_m$-Z-$(CH_2)_pCO_2C_{1-3}$ alkyl, wherein each ($CH_2$) methylene group is optionally substituted with one or two substituents selected from the group consisting of $C_{1-4}$ alkyl, fluorine, oxo, and hydroxy; and wherein said $R^1$ heteroaryl ring is optionally substituted with one substituent independently selected from the group consisting of cyano, halogen, $C_{1-4}$ alkyl, $C_{1-4}$ alkoxy, $C_{1-4}$ alkylthio, $C_{1-4}$ alkylsulfonyl, and trifluoromethyl;

each $R^2$ is independently selected from the group consisting of:
hydrogen,
halogen,
hydroxy,
cyano,
amino,
nitro,
$C_{1-4}$ alkyl, optionally substituted with one to five fluorines,
$C_{1-4}$ alkoxy, optionally substituted with one to five fluorines,
$C_{1-4}$ alkylthio, optionally substituted with one to five fluorines,
$C_{1-4}$ alkylsulfonyl,
carboxy,
$C_{1-4}$ alkyloxycarbonyl, and
$C_{1-4}$ alkylcarbonyl;

each $R^3$ is independently selected from the group consisting of:
$C_{1-6}$ alkyl,
$C_{2-6}$ alkenyl,
$(CH_2)_n$-phenyl,
$(CH_2)_n$-naphthyl,
$(CH_2)_n$-heteroaryl,
$(CH_2)_n$-heterocyclyl,
$(CH_2)_nC_{3-7}$ cycloalkyl,
halogen,
nitro,
$(CH_2)_nOR^4$,
$(CH_2)_nN(R^4)_2$,
$(CH_2)_nC\equiv N$,
$(CH_2)_nCO_2R^4$,
$(CH_2)_nNR^4SO_2R^4$
$(CH_2)_nSO_2N(R^4)_2$,
$(CH_2)_nS(O)_{0-2}R^4$,
$(CH_2)_nNR^4C(O)N(R^4)_2$,
$(CH_2)_nC(O)N(R^4)_2$,
$(CH_2)_nNR^4C(O)R^4$,
$(CH_2)_nNR^4CO_2R^4$,
$(CH_2)_nC(O)R^4$,
$O(CH_2)_nC(O)N(R^4)_2$,
$(CH_2)_s$-Z-$(CH_2)_t$-phenyl,
$(CH_2)_s$-Z-$(CH_2)_t$-naphthyl,
$(CH_2)_s$-Z-$(CH_2)_t$-heteroaryl,
$(CH_2)_s$-Z-$(CH_2)_t$-heterocyclyl,
$(CH_2)_s$-Z-$(CH_2)_t$—$C_{3-7}$ cycloalkyl,
$(CH_2)_s$-Z-$(CH_2)_t$—$OR^4$,
$(CH_2)_s$-Z-$(CH_2)_t$—$N(R^4)_2$,
$(CH_2)_s$-Z-$(CH_2)_t$—$NR^4SO_2R^4$,
$(CH_2)_s$-Z-$(CH_2)_t$—$C\equiv N$,
$(CH_2)_s$-Z-$(CH_2)_t$—$CO_2R^4$,
$(CH_2)_s$-Z-$(CH_2)_t$—$SO_2N(R^4)_2$,
$(CH_2)_s$-Z-$(CH_2)_t$—$S(O)_{0-2}R^4$,
$(CH_2)_s$-Z-$(CH_2)_t$—$NR^4C(O)N(R^4)_2$,
$(CH_2)_s$-Z-$(CH_2)_t$—$C(O)N(R^4)_2$,
$(CH_2)_s$-Z-$(CH_2)_t$—$NR^4C(O)R^4$,
$(CH_2)_s$-Z-$(CH_2)_t$—$NR^4CO_2R^4$,
$(CH_2)_s$-Z-$(CH_2)_t$—$C(O)R^4$,
$CF_3$,
$CH_2CF_3$,
$OCF_3$, and
$OCH_2CF_3$;

in which phenyl, naphthyl, heteroaryl, cycloalkyl, and heterocyclyl are optionally substituted with one to three substituents independently selected from halogen, hydroxy, $C_{1-4}$ alkyl, trifluoromethyl, and $C_{1-4}$ alkoxy; and wherein any methylene ($CH_2$) carbon atom in $R^3$ is optionally substituted with one to two groups independently selected from fluorine, hydroxy, and $C_{1-4}$ alkyl; or two substituents when on the same methylene ($CH_2$) group are taken together with the carbon atom to which they are attached to form a cyclopropyl group;
each $R^4$ is independently selected from the group consisting of
hydrogen,
$C_{1-6}$ alkyl,
$(CH_2)_n$-phenyl,
$(CH_2)_n$-heteroaryl,
$(CH_2)_n$-naphthyl, and
$(CH_2)_n C_{3-7}$ cycloalkyl;
wherein alkyl, phenyl, heteroaryl, and cycloalkyl are optionally substituted with one to three groups independently selected from halogen, trifluoromethyl, $C_{1-4}$ alkyl, and $C_{1-4}$ alkoxy; or two $R^4$ groups together with the atom to which they are attached form a 4- to 8-membered mono- or bicyclic ring system optionally containing an additional heteroatom selected from O, S, NH, and $NC_{1-4}$ alkyl;

$R^5, R^6, R^7, R^8, R^9, R^{10}, R^{11}$, and $R^{12}$ are each independently hydrogen, fluorine, or $C_{1-3}$ alkyl, wherein alkyl is optionally substituted with one to three substituents independently selected from fluorine and hydroxy;

$R^{13}$ is hydrogen, $C_{1-3}$ alkyl, fluorine, or hydroxy; and each $R^{14}$ is hydrogen or $C_{1-3}$ alkyl.

In one embodiment of the compounds of the present invention, m is 1 or 2. In a class of this embodiment, m is 1.

In a second embodiment of the compounds of the present invention, q and r are both 1, affording a 6-membered piperidine ring.

In a third embodiment of the compounds of the present invention, q is 1 and r is 0, affording a 5-membered pyrrolidine ring.

In a fourth embodiment of the compounds of the present invention, q and r are both 0, affording a 4-membered azetidine ring.

In a fifth embodiment of the compounds of the present invention, X—Y is CH—O. In a class of this embodiment, Ar is phenyl substituted with one to three $R^3$ substituents as defined above.

In a sixth embodiment of the compounds of the present invention, X—Y is CH—$S(O)_p$. In a class of this embodiment, Ar is phenyl substituted with one to three $R^3$ substituents as defined above.

In a seventh embodiment of the compounds of the present invention, X—Y is N—$CR^aR^b$. In a class of this embodiment, Ar is phenyl substituted with one to three $R^3$ substituents as defined above. In yet another class of this embodiment, $R^a$ and $R^b$ are hydrogen and Ar is phenyl substituted with one to three $R^3$ substituents.

In an eighth embodiment of the compounds of the present invention, X—Y is $CR^{13}$—$CR^aR^b$. In a class of this embodiment, Ar is phenyl substituted with one to three $R^3$ substituents as defined above. In yet another class of this embodiment, $R^a$, $R^b$, and $R^{13}$ are hydrogen and Ar is phenyl substituted with one to three $R^3$ substituents.

In a further embodiment of the compounds of the present invention, $R^5, R^6, R^7, R^8, R^9, R^{10}, R^{11}$, and $R^{12}$ are each hydrogen.

In yet a further embodiment, W is heteroaryl selected from the group consisting of:

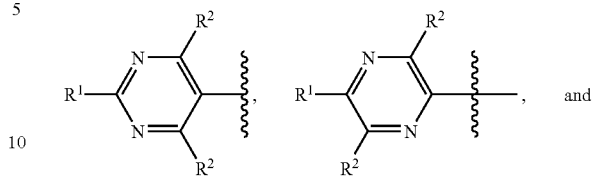

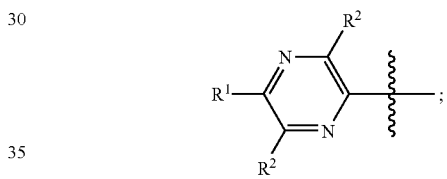

wherein $R^1$ and $R^2$ are as defined above. In a class of this embodiment, each $R^2$ is hydrogen.

In another class of this embodiment, W is

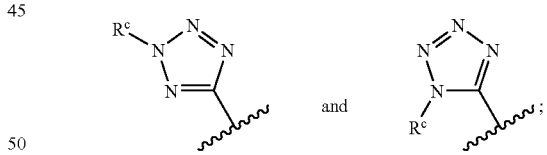

wherein $R^1$ and $R^2$ are as defined above. In a subclass of this class, each $R^2$ is hydrogen.

In a yet a further embodiment, $R^1$ is heteroaryl selected from the group consisting of:

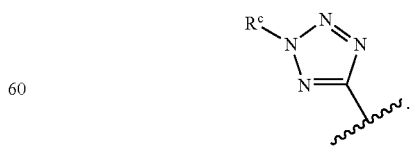

wherein $R^c$ is —$CH_2CO_2H$ or —$CH_2CO_2C_{1-13}$ alkyl. In a class of this embodiment, $R^1$ is In yet a further embodiment of the compounds of the present invention, q and r are both 1; X—Y is CH—O; W is heteroaryl selected from the group consisting of:

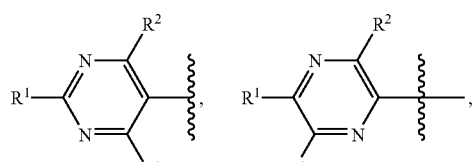

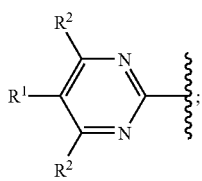

and R1 is heteroaryl selected from the group consisting of:

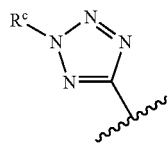 and 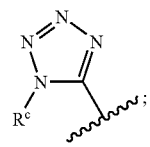;

wherein $R^c$ is —$CH_2CO_2H$ or —$CH_2CO_2C_{1-3}$ alkyl and $R^2$ is as defined above.

In a class of this embodiment, W is

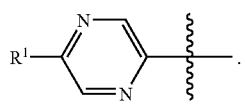.

In another class of this embodiment, $R^2$, $R^5$, $R^6$, $R^7$, $R^8$, $R^9$, $R^{10}$, $R^{11}$, and $R^{12}$ are each hydrogen.

Illustrative, but nonlimiting examples, of compounds of the present invention that are useful as inhibitors of SCD are the following:

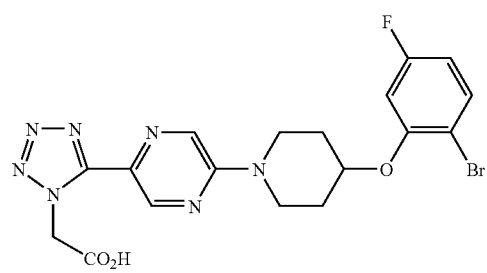

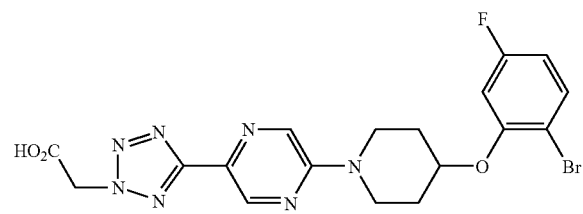

-continued

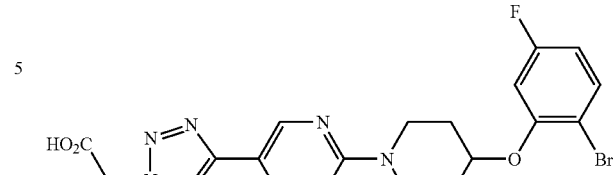

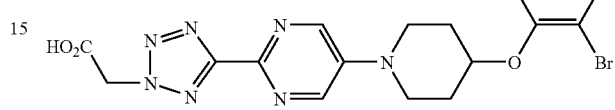

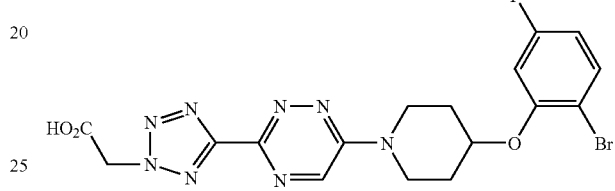

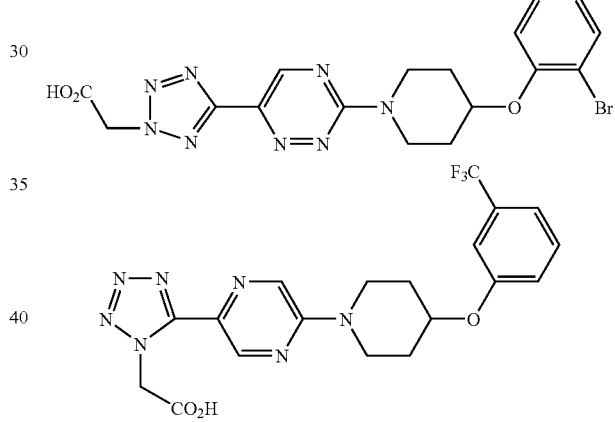

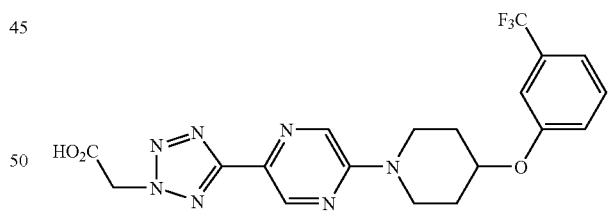

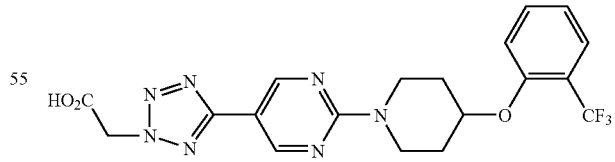

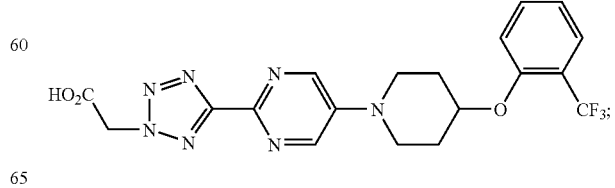

and pharmaceutically acceptable salts thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. When no number of carbon atoms is specified, $C_{1-6}$ is intended.

"Cycloalkyl" means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkenyl" shall mean straight or branched-chain alkenes having the specified number of carbon atoms. Examples of alkenyl include vinyl, 1-propenyl, 1-butenyl, 2-butenyl, and the like.

The term "alkoxy" refers to straight or branched chain alkoxides of the number of carbon atoms specified (e.g., $C_{1-6}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-6}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl (MeSO$_2$—), ethylsulfonyl, isopropylsulfonyl, etc.].

The term "alkylsulfinyl" refers to straight or branched chain alkylsulfoxides of the number of carbon atoms specified (e.g., $C_{1-6}$ alkylsulfinyl), or any number within this range [i.e., methylsulfinyl (MeSO—), ethylsulfinyl, isopropylsulfinyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, 2-oxopiperidin-1-yl, 2-oxopyrrolidin-1-yl, and 2-oxoazetidin-1-yl, and the like.

"Heteroaryl" means an aromatic or partially aromatic heterocycle that contains at least one ring heteroatom selected from O, S and N. Heteroaryls thus includes heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl (in particular, 1,3,4-oxadiazol-2-yl and 1,2,4-oxadiazol-3-yl), thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

Compounds of structural formula I may contain one or more asymmetric centers and can thus occur as racemates and racemic mixtures, single enantiomers, diastereomeric mixtures and individual diastereomers. The present invention is meant to comprehend all such isomeric forms of the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetyl, pivaloyl, benzoyl, and aminoacyl, can be employed. Included are those esters and acyl groups known in the art for modifying the solubility or hydrolysis characteristics for use as sustained-release or prodrug formulations.

Solvates, in particular hydrates, of the compounds of structural formula I are included in the present invention as well.

The subject compounds are useful in a method of inhibiting the stearoyl-coenzyme A delta-9 desaturase enzyme (SCD) in a patient such as a mammal in need of such inhibition comprising the administration of an effective amount of the compound. The compounds of the present invention are therefore useful to control, prevent, and/or treat conditions and diseases mediated by high or abnormal SCD enzyme activity.

Thus, one aspect of the present invention concerns a method of treating hyperglycemia, diabetes or insulin resistance in a mammalian patient in need of such treatment, which comprises administering to said patient an effective amount of a compound in accordance with structural formula I or a pharmaceutically salt or solvate thereof.

A second aspect of the present invention concerns a method of treating non-insulin dependent diabetes mellitus (Type 2 diabetes) in a mammalian patient in need of such treatment comprising administering to the patient an antidiabetic effective amount of a compound in accordance with structural formula I.

A third aspect of the present invention concerns a method of treating obesity in a mammalian patient in need of such treatment comprising administering to said patient a compound in accordance with structural formula I in an amount that is effective to treat obesity.

A fourth aspect of the invention concerns a method of treating metabolic syndrome and its sequelae in a mammalian patient in need of such treatment comprising administering to said patient a compound in accordance with structural formula I in an amount that is effective to treat metabolic syndrome and its sequelae. The sequelae of the metabolic syndrome include hypertension, elevated blood glucose levels, high triglycerides, and low levels of HDL cholesterol.

A fifth aspect of the invention concerns a method of treating a lipid disorder selected from the group consisting of dyslipidemia, hyperlipidemia, hypertriglyceridemia, hypercholesterolemia, low HDL and high LDL in a mammalian patient in need of such treatment comprising administering to said patient a compound in accordance with structural formula I in an amount that is effective to treat said lipid disorder.

A sixth aspect of the invention concerns a method of treating atherosclerosis in a mammalian patient in need of such treatment comprising administering to said patient a compound in accordance with structural formula I in an amount effective to treat atherosclerosis.

A seventh aspect of the invention concerns a method of treating cancer in a mammalian patient in need of such treatment comprising administering to said patient a compound in accordance with structural formula I in an amount effective to treat cancer.

A further aspect of the invention concerns a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) fatty liver disease, (21) polycystic ovary syndrome, (22) sleep-disordered breathing, (23) metabolic syndrome, and (24) other conditions and disorders where insulin resistance is a component, in a mammalian patient in need of such treatment comprising administering to the patient a compound in accordance with structural formula I in an amount that is effective to treat said condition.

Yet a further aspect of the invention concerns a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) fatty liver disease, (21) polycystic ovary syndrome, (22) sleep-disordered breathing, (23) metabolic syndrome, and (24) other conditions and disorders where insulin resistance is a component, and other conditions and disorders where insulin resistance is a component, in a mammalian patient in need of such treatment comprising administering to the patient a compound in accordance with structural formula I in an amount that is effective to delay the onset of said condition.

Yet a further aspect of the invention concerns a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) fatty liver disease, (21) polycystic ovary syndrome, (22) sleep-disordered breathing, (23) metabolic syndrome, and (24) other conditions and disorders where insulin resistance is a component, in a mammalian patient in need of such treatment comprising administering to the patient a compound in accordance with structural formula I in an amount that is effective to reduce the risk of developing said condition.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent, such as a mouse, species can be treated. However, the method can also be practiced in other species, such as avian species (e.g., chickens).

The present invention is further directed to a method for the manufacture of a medicament for inhibiting stearoyl-coenzyme A delta-9 desaturase enzyme activity in humans and animals comprising combining a compound of the present invention with a pharmaceutically acceptable carrier or diluent. More particularly, the present invention is directed to the use of a compound of structural formula I in the manufacture of a medicament for use in treating a condition selected from the group consisting of hyperglycemia, Type 2 diabetes, insulin resistance, obesity, and a lipid disorder in a mammal, wherein the lipid disorder is selected from the group consisting of dyslipidemia, hyperlipidemia, hypertriglyceridemia, hypercholesterolemia, low HDL, and high LDL.

The subject treated in the present methods is generally a mammal, preferably a human being, male or female, in whom inhibition of stearoyl-coenzyme A delta-9 desaturase enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of stearoyl-coenzyme A delta-9 desaturase (SCD) enzyme activity may be demonstrated by the following microsomal and whole-cell based assays:

I. SCD-Induced Rat Liver Microsome Assay:

The activity of compounds of formula I against the SCD enzyme is determined by following the conversion of radiolabeled-stearoyl-CoA to oleoyl-CoA using SCD 1-induced rat liver microsome and a previously published procedure with some modifications (Joshi, et al., *J. Lipid Res.*, 18: 32-36 (1977)). After feeding wistar rats with a high carbohydrate/fat-free rodent diet (LabDiet # 5803, Purina) for 3 days, the SCD-induced livers were homogenized (1:10 w/v) in 250 mM sucrose, 1 mM EDTA, 5 mM DTT and 50 mM Tris-HCl (pH 7.5). After a 20 min centrifugation (18,000×g/4° C.) to remove tissue and cell debris, the microsome was prepared by a 100,000×g centrifugation (60 min) with the resulting pellet suspended in 100 mM sodium phosphate, 20% glycerol and 2 mM DTT. Test compound in 2 µL DMSO was incubated for 15 min. at room temperature with 180 µL of the microsome (typically at about 100 µg/mL, in Tris-HCl buffer (100 mM, pH 7.5), ATP (5 mM), Coenzyme A (0.1 mM), Triton X-100 (0.5 mM) and NADH (2 mM)). The reaction was initiated by the addition of 20 µL of [$^3$H]-Stearoyl-CoA (final concentration at 2 µM with the radioactivity concentration at 1 µCi/mL), and terminated by the addition of 150 µL of 1N sodium hydroxide. After 60 min at room temperature to hydrolyze the oleoyl-CoA and stearoyl-CoA, the solution was acidified by the addition of 150 µL of 15% phosphoric acid (v/v) in ethanol supplemented with 0.5 mg/mL stearic acid and 0.5 mg/mL oleic acid. [$^3$H]-oleic acid and [$^3$H]-stearic acid were then quantified on a HPLC that is equipped with a C-18 reverse phase column and a Packard Flow Scintillation Analyzer. Alternatively, the reaction mixture (80 µL) was mixed with a calcium chloride/charcoal aqueous suspension (100 µL of 15% (w/v) charcoal plus 20 µL of 2 N $CaCl_2$). The resulting mixture was centrifuged to precipitate the radioactive fatty acid species into a stable pellet. Tritiated water from SCD-catalyzed desaturation of 9,10-[$^3$H]-stearoyl-CoA was quantified by counting 50 µL of the supernant on a scintillation counter.

II. Whole Cell-based SCD (Delta-9). Delta-5 and Delta-6 Desaturase Assays:

Human HepG2 cells were grown on 24-well plates in MEM media (Gibco cat# 11095-072) supplemented with 10% heat-inactivated fetal bovine serum at 37° C. under 5% $CO_2$ in a humidified incubator. Test compound dissolved in the media was incubated with the subconfluent cells for 15 min at 37° C. [1-$^{14}$C]-stearic acid was added to each well to a final concentration of 0.05 µCi/mL to detect SCD-catalyzed [$^{14}$C]-oleic acid formation. 0.05 µCi/mL of [1-$^{14}$C]-eicosatrienoic acid or [1-$^{14}$C]-linolenic acid plus 10 µM of 2-amino-N-(3-chlorophenyl)benzamide (a delta-5 desaturase inhibitor) was used to index the delta-5 and delta-6 desaturase activities, respectively. After 4 h incubation at 37° C., the culture media was removed and the labeled cells were washed with PBS (3×1 mL) at room temperature. The labeled cellular lipids were hydrolyzed under nitrogen at 65° C. for 1 h using 400 µL of 2 N sodium hydroxide plus 50 µL of L-α-phosphatidylcholine (2 mg/mL in isopropanol, Sigma #P-3556). After acidification with phosphoric acid (60 µL), the radioactive species were extracted with 300 µL of acetonitrile and quantified on a HPLC that was equipped with a C-18 reverse phase column and a Packard Flow Scintillation Analyzer. The levels of [$^{14}$C]-oleic acid over [$^{14}$C]-stearic acid, [$^{14}$C]-arachidonic acid over [$^{14}$C]-eicosatrienoic acid, and [$^{14}$C]-eicosatetraenoic acid (8,11,14,17) over [$^{14}$C]-linolenic acid were used as the corresponding activity indices of SCD, delta-5 and delta-6 desaturase, respectively.

The SCD inhibitors of formula I, particularly the inhibitors of Examples 1 to 23, exhibit an inhibition constant IC$_{50}$ of less than 1 μM and more typically less than 0.1 μM. Generally, the IC$_{50}$ ratio for delta-5 or delta-6 desaturases to SCD for a compound of formula I, particularly for Examples 1 to 23, is at least about ten or more, and preferably about one hundred or more.

In Vivo Efficacy of Compounds of the Present Invention:

The in vivo efficacy of compounds of formula I was determined by following the conversion of [1-$^{14}$C]-stearic acid to [1-$^{14}$C]oleic acid in animals as exemplified below. Mice were dosed with a compound of formula I and one hour later the radioactive tracer, [1-$^{14}$C]-stearic acid, was dosed at 20 μCi/kg IV. At 3 h post dosing of the compound, the liver was harvested and then hydrolyzed in 10 N sodium hydroxide for 24 h at 80° C., to obtain the total liver fatty acid pool. After phosphoric acid acidification of the extract, the amount of [1-$^{14}$C]-stearic acid and [1-$^{14}$C]-oleic acid was quantified on a HPLC that was equipped with a C-18 reverse phase column and a Packard Flow Scintillation Analyzer.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of formula I, and either administered separately or in the same pharmaceutical composition, include, but are not limited to:

(a) dipeptidyl peptidase-IV (DPP-4) inhibitors;

(b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, Galida, TAK-559, PPARα agonists, such as fenofibric acid derivatives (gemfibrozil, clofibrate, fenofibrate and bezafibrate), and selective PPARγ modulators (SPPARγM's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide, glyburide, glipizide, glimepiride, and meglitinides, such as nateglinide and repaglinide;

(e) α-glucosidase inhibitors (such as acarbose and miglitol);

(f) glucagon receptor antagonists, such as those disclosed in WO 98/04528, WO 99/01423, WO 00/39088, and WO 00/69810;

(g) GLP-1, GLP-1 analogues or mimetics, and GLP-1 receptor agonists, such as exendin-4 (exenatide), liraglutide (N,N-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA: cholesterol acyltransferase inhibitors, such as avasimibe, and (viii) antioxidants, such as probucol;

(k) PPARδ agonists, such as those disclosed in WO 97/28149;

(l) antiobesity compounds, such as fenfluramine, dexfenfluramine, phentermine, sibutramine, orlistat, neuropeptide Y$_1$ or Y$_5$ antagonists, CB1 receptor inverse agonists and antagonists, β$_3$ adrenergic receptor agonists, melanocortin-receptor agonists, in particular melanocortin-4 receptor agonists, ghrelin antagonists, bombesin receptor agonists (such as bombesin receptor subtype-3 agonists), and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(p) glucokinase activators (GKAs), such as those disclosed in WO 03/015774; WO 04/076420; and WO 04/081001;

(q) inhibitors of 11β-hydroxysteroid dehydrogenase type 1, such as those disclosed in U.S. Pat. No. 6,730,690; WO 03/104207; and WO 04/058741;

(r) inhibitors of cholesteryl ester transfer protein (CETP), such as torcetrapib;

(s) inhibitors of fructose 1,6-bisphosphatase, such as those disclosed in U.S. Pat. Nos. 6,054,587; 6,110,903; 6,284,748; 6,399,782; and 6,489,476;

(t) acetyl CoA carboxylase-1 and/or -2 inhibitors;

(u) AMPK activators; and (v) agonists of GPR-119.

Dipeptidyl peptidase-IV inhibitors that can be combined with compounds of structural formula I include those disclosed in U.S. Pat. No. 6,699,871; WO 02/076450 (3 Oct. 2002); WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); WO 03/082817 (9 Oct. 2003); WO 03/000181 (3 Jan. 2003); WO 04/007468 (22 Jan. 2004); WO 04/032836 (24 Apr. 2004); WO 04/037169 (6 May 2004); and WO 04/043940 (27 May 2004). Specific DPP-IV inhibitor compounds include sitagliptin (MK-0431); vildagliptin (LAF 237); denagliptin; P93/01; saxagliptin (BMS 477118); RO0730699; MP513; SYR-322: ABT-279; PHX1149; GRC-8200; and TS021.

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, bombesin receptor agonists, and melanin-concentrating hormone (MCH) receptor antagonists. For a review of antiobesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs,"*Expert Opin. Emerging Drugs*, 8: 217-237 (2003); and J. A. Fernandez-Lopez, et al., "Pharmacological Approaches for the Treatment of Obesity," *Drugs*, 62: 915-944 (2002).

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; U.S. Pat. No. 5,292, 736; PCT Publication WO 03/086288; PCT Publication WO 03/087037; PCT Publication WO 04/048317; PCT Publication WO 03/007887; PCT Publication WO 03/063781; PCT Publication WO 03/075660; PCT Publication WO 03/077847; PCT Publication WO 03/082190; PCT Publication WO 03/082191; PCT Publication WO 03/087037; PCT Publication WO 03/086288; PCT Publication WO 04/012671; PCT Publication WO 04/029204; PCT Publication WO 04/040040; PCT Publication WO 01/64632; PCT Publication WO 01/64633; and PCT Publication WO 01/64634.

Melanocortin-4 receptor (MC4R) agonists useful in the present invention include, but are not limited to, those disclosed in U.S. Pat. Nos. 6,294,534, 6,350,760, 6,376,509, 6,410,548, 6,458,790, 6,472,398, 5,837,521, 6,699,873, which are hereby incorporated by reference in their entirety; in US Patent Application Publication Nos. US 2002/0004512, US2002/0019523, US2002/0137664, US2003/0236262, US2003/0225060, US2003/0092732, US2003/109556, US 2002/0177151, US 2002/187932, US 2003/0113263, which are hereby incorporated by reference in their entirety; and in WO 99/64002, WO 00/74679, WO 02/15909, WO 01/70708, WO 01/70337, WO 01/91752, WO 02/068387, WO 02/068388, WO 02/067869, WO 03/007949, WO 2004/024720, WO 2004/089307, WO 2004/078716, WO 2004/078717, WO 2004/037797, WO 01/58891, WO 02/070511, WO 02/079146, WO 03/009847, WO 03/057671, WO 03/068738, WO 03/092690, WO 02/059095, WO 02/059107, WO 02/059108, WO 02/059117, WO 02/085925, WO 03/004480, WO 03/009850, WO 03/013571, WO 03/031410, WO 03/053927, WO 03/061660, WO 03/066597, WO 03/094918, WO 03/099818, WO 04/037797, WO 04/048345, WO 02/018327, WO 02/080896, WO 02/081443, WO 03/066587, WO 03/066597, WO 03/099818, WO 02/062766, WO 03/000663, WO 03/000666, WO 03/003977, WO 03/040107, WO 03/040117, WO 03/040118, WO 03/013509, WO 03/057671, WO 02/079753, WO 02//092566, WO 03/-093234, WO 03/095474, and WO 03/104761.

One particular aspect of combination therapy concerns a method of treating a condition selected from the group consisting of hypercholesterolemia, atherosclerosis, low HDL levels, high LDL levels, hyperlipidemia, hypertriglyceridemia, and dyslipidemia, in a mammalian patient in need of such treatment comprising administering to the patient a therapeutically effective amount of a compound of structural formula I and an HMG-CoA reductase inhibitor.

More particularly, this aspect of combination therapy concerns a method of treating a condition selected from the group consisting of hypercholesterolemia, atherosclerosis, low HDL levels, high LDL levels, hyperlipidemia, hypertriglyceridemia and dyslipidemia in a mammalian patient in need of such treatment wherein the HMG-CoA reductase inhibitor is a statin selected from the group consisting of lovastatin, simvastatin, pravastatin, cerivastatin, fluvastatin, atorvastatin, and rosuvastatin.

In another aspect of the invention, a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions is disclosed comprising administering to a mammalian patient in need of such treatment a therapeutically effective amount of a compound of structural formula I and an HMG-CoA reductase inhibitor.

In another aspect of the invention, a method for delaying the onset or reducing the risk of developing atherosclerosis in a human patient in need of such treatment is disclosed comprising administering to said patient an effective amount of a compound of structural formula I and an HMG-CoA reductase inhibitor.

More particularly, a method for delaying the onset or reducing the risk of developing atherosclerosis in a human patient in need of such treatment is disclosed, wherein the HMG-CoA reductase inhibitor is a statin selected from the group consisting of: lovastatin, simvastatin, pravastatin, cerivastatin, fluvastatin, atorvastatin, and rosuvastatin.

In another aspect of the invention, a method for delaying the onset or reducing the risk of developing atherosclerosis in a human patient in need of such treatment is disclosed, wherein the HMG-Co A reductase inhibitor is a statin and further comprising administering a cholesterol absorption inhibitor.

More particularly, in another aspect of the invention, a method for delaying the onset or reducing the risk of developing atherosclerosis in a human patient in need of such treatment is disclosed, wherein the HMG-Co A reductase inhibitor is a statin and the cholesterol absorption inhibitor is ezetimibe.

In another aspect of the invention, a pharmaceutical composition is disclosed which comprises:

(1) a compound of structural formula I;
(2) a compound selected from the group consisting of:
  (a) dipeptidyl peptidase IV (DPP-IV) inhibitors;
  (b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, Galida, TAK-559, PPARα agonists, such as fenofibric acid derivatives (gemfibrozil, clofibrate, fenofibrate and bezafibrate), and selective PPARγ modulators (SPPARγM's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors;
  (c) insulin or insulin mimetics;
  (d) sulfonylureas and other insulin secretagogues, such as tolbutamide, glyburide, glipizide, glimepiride, and meglitinides, such as nateglinide and repaglinide;
  (e) α-glucosidase inhibitors (such as acarbose and miglitol);
  (f) glucagon receptor antagonists, such as those disclosed in WO 98/04528, WO 99/01423, WO 00/39088, and WO 00/69810;
  (g) GLP-1, GLP-1 analogues or mimetics, and GLP-1 receptor agonists, such as exendin-4 (exenatide), liraglutide (N,N-2211), CJC-1131, LY-307161, and those disclosed in WO 00/42026 and WO 00/59887;
  (h) GIP and GIP mimetics, such as those disclosed in WO 00/58360, and GIP receptor agonists;
  (i) PACAP, PACAP mimetics, and PACAP receptor agonists such as those disclosed in WO 01/23420;
  (j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA: cholesterol acyl-transferase inhibitors, such as avasimibe, and (viii) antioxidants, such as probucol;
  (k) PPARδ agonists, such as those disclosed in WO 97/28149;
  (l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, β3 adrenergic receptor agonists, melanocortin-receptor agonists, in particular melanocortin-4 receptor agonists, ghrelin antagonists, bombesin receptor agonists (such as bombesin receptor subtype-3 agonists), and melanin-concentrating hormone (MCH) receptor antagonists;
  (m) ileal bile acid transporter inhibitors;
  (n) agents intended for use in inflammatory conditions such as aspirin, non-steroidal anti-inflammatory drugs (NSAIDs), glucocorticoids, azulfidine, and selective cyclooxygenase-2 (COX-2) inhibitors;
  (o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;
  (p) glucokinase activators (GKAs), such as those disclosed in WO 03/015774; WO 04/076420; and WO 04/081001;
  (q) inhibitors of 11β-hydroxysteroid dehydrogenase type 1, such as those disclosed in U.S. Pat. No. 6,730,690; WO 03/104207; and WO 04/058741;
  (r) inhibitors of cholesteryl ester transfer protein (CETP), such as torcetrapib;
  (s) inhibitors of fructose 1,6-bisphosphatase, such as those disclosed in U.S. Pat. Nos. 6,054,587; 6,110,903; 6,284,748; 6,399,782; and 6,489,476;
  (t) acetyl CoA carboxylase-1 and/or -2 inhibitors;
  (u) AMPK activators; and
  (v) agonists of GPR 119; and
(3) a pharmaceutically acceptable carrier.

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of stearoyl-CoA delta-9 desaturase enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 0.250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

List of Abbreviations:
Alk=alkyl
APCI=atmospheric pressure chemical ionization
Ar=aryl
Boc=tert-butoxycarbonyl
br=broad
d=doublet
DBU=1,8-diazabicyclo[5.4.0]undec-7-ene
DMF=N,N-dimethylformamide
DAST=diethylaminosulfur trifluoride
Deoxofluore®=bis(2-methoxyethyl)aminosulfur trifluoride
DIBAL-H=diisobutylaluminum hydride
DMSO=dimethyl sulfoxide
ESMS=electrospray ion-mass spectroscopy
EtOAc=ethyl acetate
m=multiplet
m-CPBA=3-chloroperoxybenzoic acid
MeOH=methyl alcohol
MS=mass spectroscopy
NaHMDS=sodium bis(trimethylsilyl)amide
NMP=1-methyl-2-pyrrolidinone
NMR=nuclear magnetic resonance spectroscopy
PG=protecting group
rt=room temperature
s=singlet
t=triplet
TFFA=trifluoroacetic anhydride
THF=tetrahydrofuran
TLC=thin-layer chromatography
TsOH=toluene-4-sulfonic acid Preparation of Compounds of the Invention:

The compounds of structural formula I can be prepared according to the procedures of the following Schemes and Examples, using appropriate materials and are further exemplified by the following specific examples. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted. Mass spectra (MS) were measured by electrospray ion-mass spectroscopy (ESMS).

Method A:

A Mitsunobu reaction using tert-butyl 4-hydroxy-1-piperidinecarboxylate 1 and 2-bromo-5-fluorophenol 2 in the presence of triphenylphosphine and tert-butyl azodicarboxylate affords the coupled product 3.

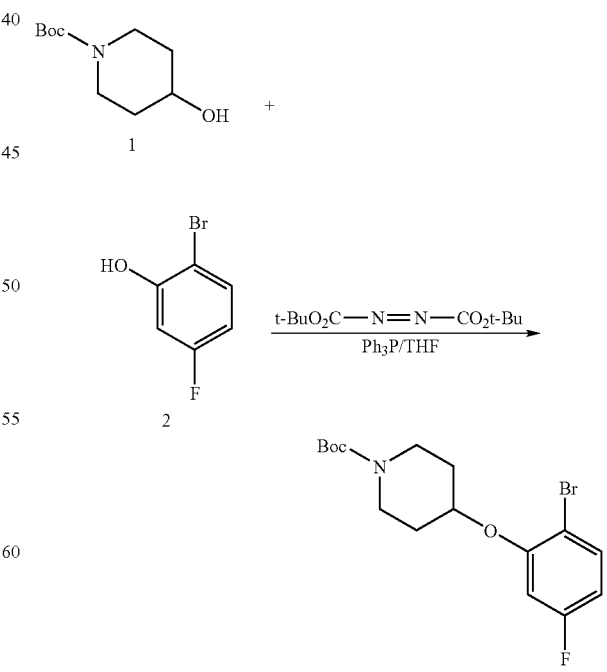

Method B:

tert-Butyl 4-hydroxy-1-piperidinecarboxylate 1 and 2-bromo-1,5-difluorobenzene 4 are treated with potassium tert-butoxide in dioxane to give the coupled product 3.

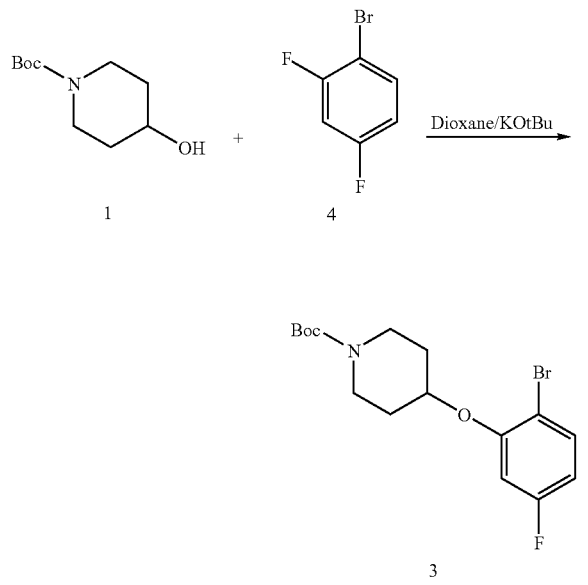

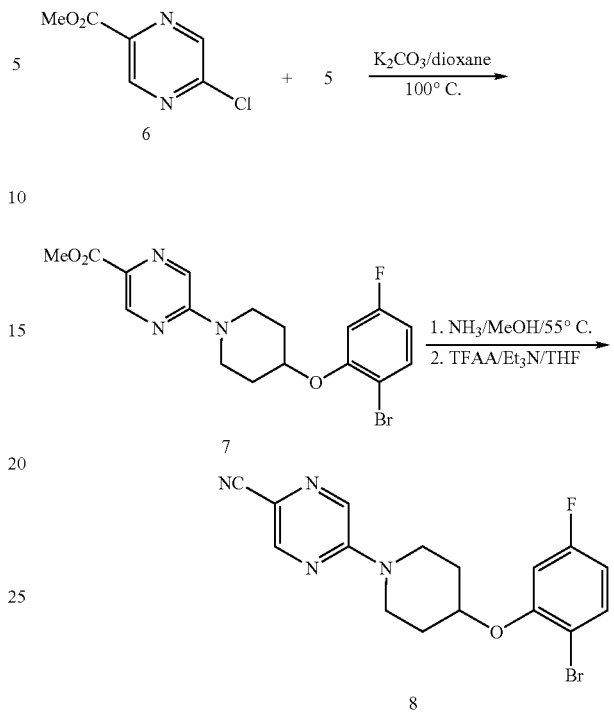

Method C:

The intermediate 3 can then be converted to the free amine 5 by treatment with HCl in dioxane.

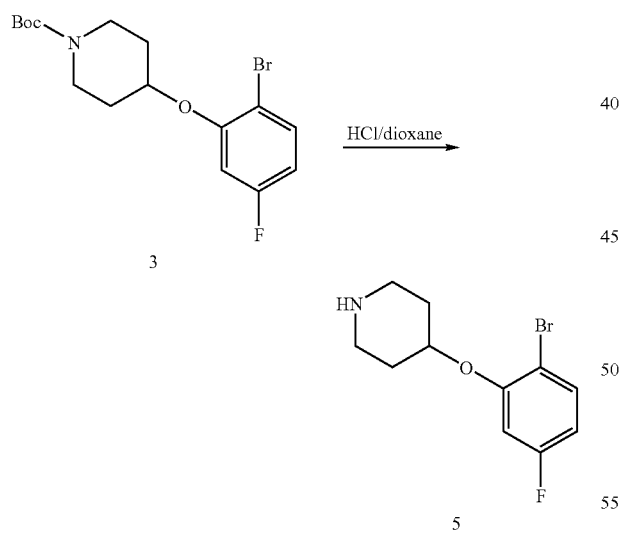

Method D:

A mixture containing the amine 5, methyl 5-chloropyrazine-2-carboxylate 6 and potassium carbonate in dioxane are heated at 100° C. for 2 h to provide the ester 7. To a suspension of ester 7 in MeOH, in a sealed tube, is bubbled ammonia gas at 0° C. and the mixture is heated at 55° C. for several days to give the amide which in turn is treated with trifluoroacetic anhydride and triethylamine in THF to provide nitrile 8.

Method E:

The nitrile 8 can be converted to the tetrazole 9 by treatment with sodium azide and ammonium chloride. Alternatively, trimethylsilyl azide or tributyltin azide can be also used.

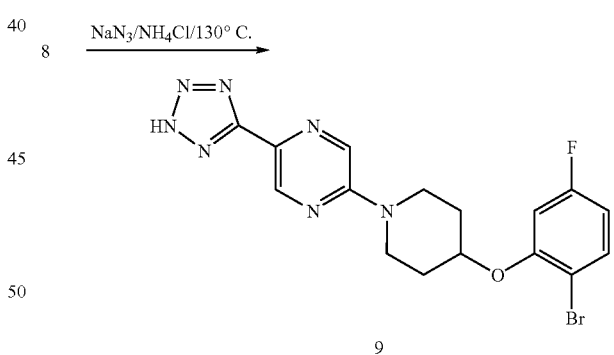

Method F:

The tetrazole 9 can be converted to the two tetrazoleacetic acid regioisomers 10 and 11 by treatment with ethyl bromoacetate and sodium hydride in DMF followed by hydrolysis of the ester. The two regioisomers can be separated by column chromatography at the ester stage.

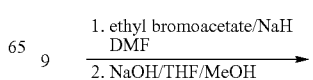

-continued

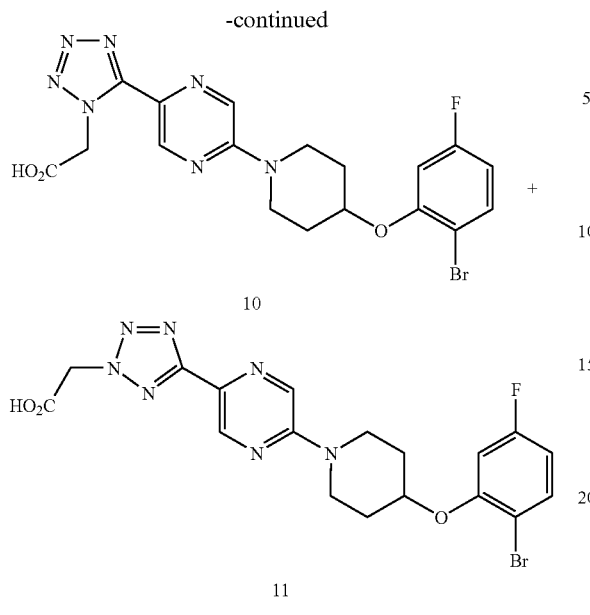

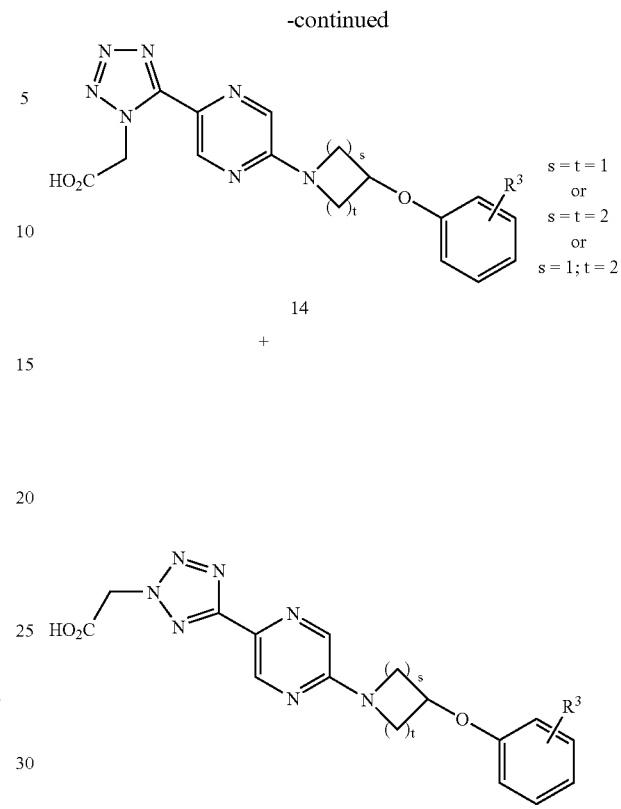

s = t = 1 or
s = t = 2 or
s = 1; t = 2

Method G:

Methods A and B can be applied to other cyclic amines such as 12 to provide amines 13 which can be converted to tetrazoles 14 and 15 using Methods C to F.

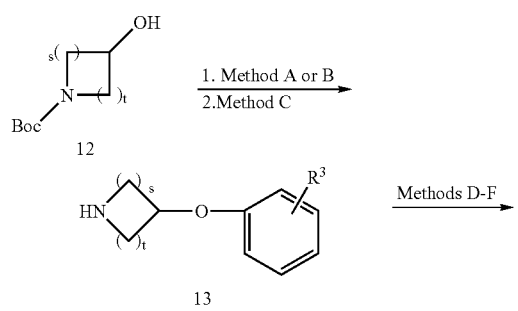

Method H:

Methods F and G can be extended to provide longer alkanoic acid side chains on the tetrazole by using the appropriate esters or acrylates. In addition, chain extension can be made directly from 11 by reducing the ester, brominating the resultant alcohol followed by cyanide displacement and hydrolysis to the acid. This process can be repeated to provide extended alkanoic acids 11b.

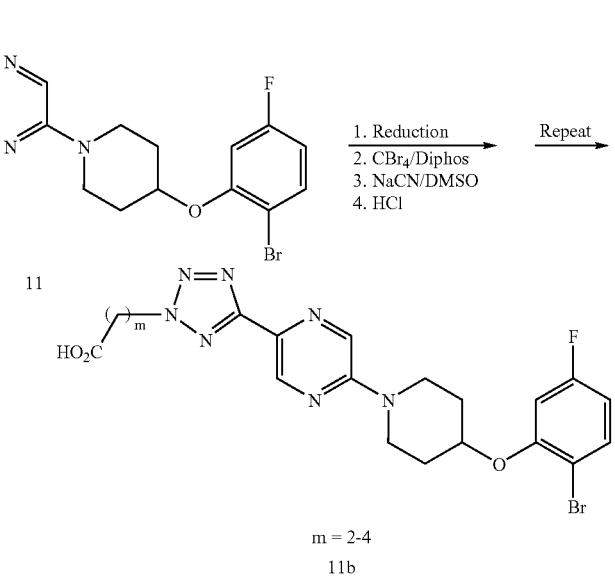

m = 2-4
11b

Method I:

A dihalogenopyrazine, pyrimidine or triazine 16 can be treated with amine 13 in the presence of a base such as potassium carbonate in dioxane or DBU in 2-propanol to provide the heteroaryl intermediate 17 which in turn can be converted to the azide 18 with sodium azide and copper iodide. Subsequently, the azide can be converted to the triazole 19 using 3-butyn-1-ol, CuI and sodium ascorbate. The alcohol can be oxidized to the aldehyde using Swern conditions followed by oxidation to the acid 20 using NaClO$_2$ in phosphate buffer.

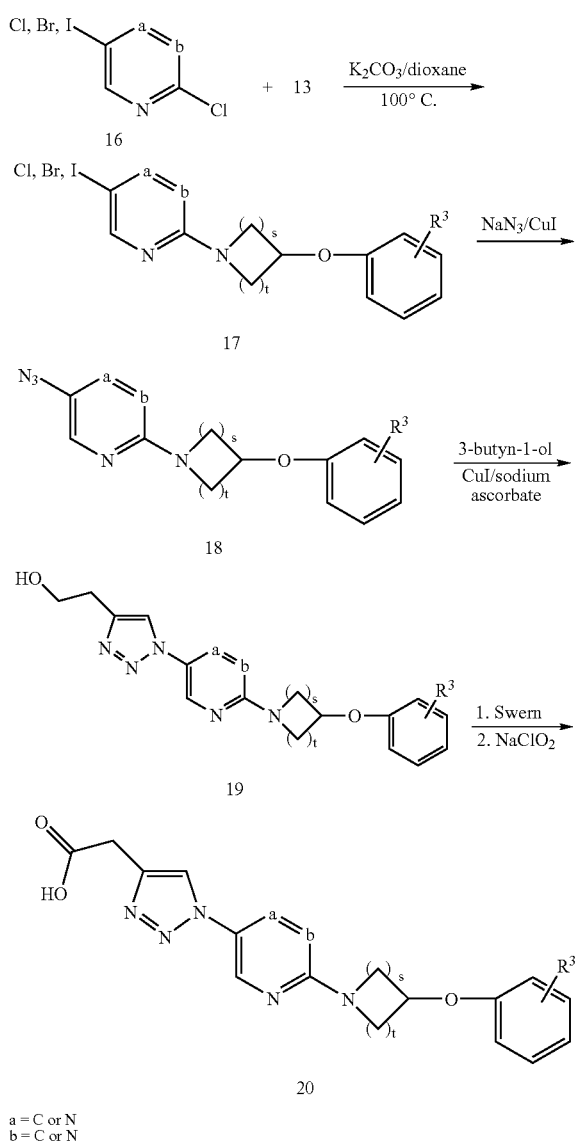

a = C or N
b = C or N

Method J:

Coupling of pyrazole 21 with the boronate 22 using a palladium source in the presence of a base such as sodium carbonate in a solvent such as DMF provides compound 23 after basic hydrolysis.

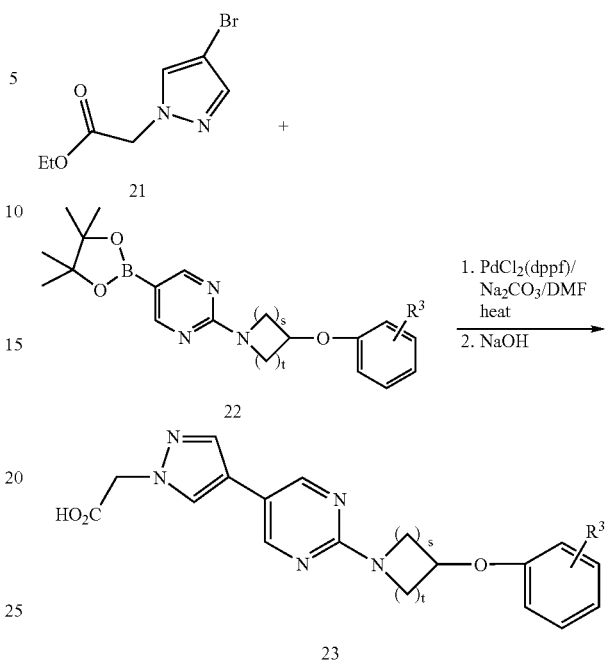

Method K:

Method D can be extended to other type of cyclic amines to provide ester 25 which can be converted to heteroarylalkanoic acids as described in the previous methods.

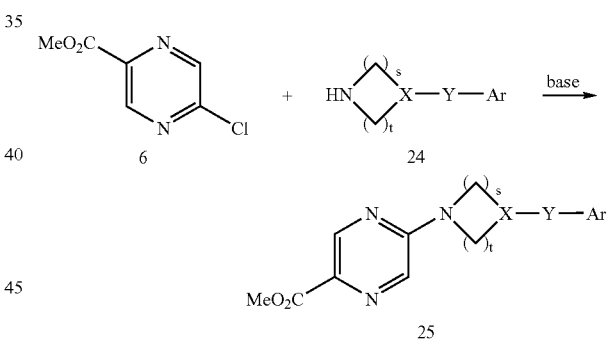

Method L:

5-Bromo-2-chloropyrimidine 26 is reacted with an appropriately substituted cyclic amine 27 in the presence of a base such as triethylamine and in a solvent, such as ethanol, to afford the bromo adduct 28. Reaction of bromide 28 with copper(I) cyanide in a solvent such as DMF under refluxing conditions gives the cyano compound 29. Reaction of cyano compound 29 with sodium azide in the presence of ammonium chloride in a solvent such as DMF under refluxing condition gives the tetrazole derivative 30. Alkylation of the tetrazole 30 with a haloalkylcarboxylic acid ester, such as ethyl bromoacetate, in the presence of a base, such as triethylamine and sodium hydride, in a solvent, such as THF, gives the tetrazole acetate regiomers 31 and 32 which can be separated by flash column chromatography or recrystallization. The ester group can be hydrolysed with aqueous NaOH in a solvent such as THF and MeOH at a temperature range of about room temperature to about refluxing temperature followed by extractive work up and purification by flash column chromatography or recrystallization to afford the heteroaryl tetrazoleacetic acid 34.

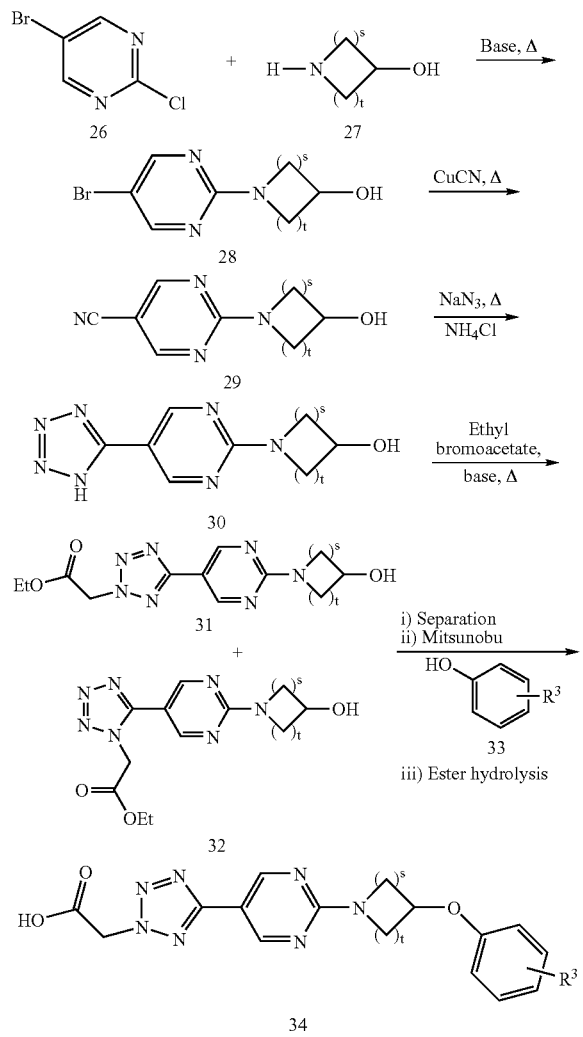

The following Examples are provided to illustrate the invention and are not to be construed as limiting the scope of the invention in any manner.

EXAMPLE 1

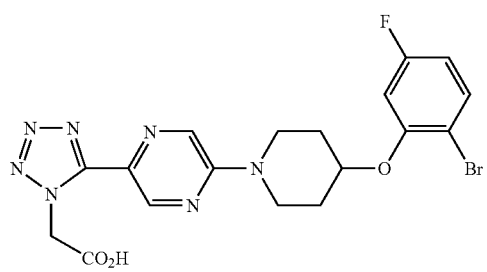

Step 1: tert-Butyl 4-(2-bromo-5-fluorophenoxy)piperidine-1-carboxylate

Method (i):

To a solution of tert-butyl 4-hydroxy-1-piperidinecarboxylate (50.6 g, 251 mmol) and di-tert-butyl azodicarboxylate (71 g, 308 mmol) in THF (350 mL) was added 2-bromo-5-fluorophenol (36 mL, 324 mmol). The mixture was cooled to −78° C. and a solution of triphenylphosphine (81.5 g, 311 mmol) in dichloromethane (130 mL) was added via cannula. After a period of 18 h at room temperature, the solvent was removed under vacuum to give the title compound as an oil which was used without further purification in Step 2.

Method (ii):

To potassium tert-butoxide (109 g, 974 mmol) in dioxane (800 mL) was added tert-butyl 4-hydroxy-1-piperidinecarboxylate (200 g, 994 mmol) followed by 1-bromo-2,4-difluorobenzene (182 g, 994 mmol). After a period of 10 h at 60° C., the reaction mixture was partitioned between water and tert-butyl methyl ether. The organic solvent was washed with brine, dried over magnesium sulfate and evaporated to give a residue which was used without purification in Step 2.

Step 2: 4-(2-Bromo-5-fluorophenoxy)piperidine tert-Butyl 4-(2-bromo-5-fluorophenoxy)piperidine-1-carboxylate from Step 1, Method (i), was dissolved in ethanol (200 mL), cooled to −78° C. and treated with 4 N HCl in dioxane (450 mL). The reaction was warmed and stirred overnight at room temperature. The solvent was removed under reduced pressure and the mixture partitioned between 1 N NaOH (750 mL) and a 1:1 mixture of ether-hexane. After several extractions, the organics layers were combined and evaporated to dryness. The crude material was dissolved in heptane (1 L) and a white precipitate was filtered and discarded. The heptane layer was diluted with ether and treated with 4 N HCl in dioxane (100 mL). The resulting precipitate was collected by filtration and washed three times with a 1:1 mixture of ether-hexane. The salt was partitioned again between 1 N NaOH (500 mL) and a 1:1 mixture of ether-hexane. After several extractions, the organic layers were combined, washed with brine, dried over magnesium sulfate, filtered and evaporated. The crude material was dissolved into heptane (2 L) and washed four times with 1 N NaOH (250 mL). The organic layer was washed with brine, dried over magnesium sulfate, filtered and evaporated to give the title compound as colorless oil.

Alternatively, tert-butyl 4-(2-bromo-5-fluorophenoxy)piperidine-1-carboxylate from Step 1, Method (ii), was dissolved in formic acid (600 mL) and warmed to reflux temperature. After a period of 45 min, the reaction mixture was concentrated and the residue partitioned between aqueous NaOH and tert-butyl methyl ether. The organic layer was washed with brine, dried over magnesium sulfate and filtered. The filtrate was then treated with 2 N HCl in ether (550 mL). After a period of 10 h, the mixture was filtered and the solid washed with ether and dried in a vacuum oven at 50° C. for 2 h to provide the title compound as the HCl salt. The salt (1.00 g, 3.22 mmol) was then partitioned between ethyl acetate and 1 N NaOH. The organic phase was separated, dried over sodium sulfate, filtered and evaporated to give the title compound as an oil.

Step 3: Methyl 5-[4-(2-bromo-5-fluorophenoxy) piperidin-1-yl]pyrazine-2-carboxylate A mixture of 4-(2-bromo-5-fluorophenoxy)piperidine from Step 2 (1.90 g, 6.95 mmol), methyl 5-chloropyrazine-2-carboxylate (1.00 g, 5.79 mmol) and potassium carbonate (1.60 g, 11.59 mmol) in dioxane (30 mL) was heated at 100° C. After a period of 2 h, the reaction mixture was partitioned between ethyl acetate and saturated aqueous ammonium chloride. The solvent was separated, dried over sodium sulfate and evaporated. The title compound was purified by flash chromatography (50% ethyl acetate in hexane) to provide the title compound.

Step 4: 5-[4-(2-Bromo-5-fluorophenoxy)piperidin-1-yl]pyrazine-2-carboxamide

A methanol (30 mL) suspension of methyl 5-[4-(2-bromo-5-fluorophenoxy)piperidin-1-yl]pyrazine-2-carboxylate from Step 3 (2.00 g, 4.87 mmol) in a sealed tube was saturated with ammonia gas at 0° C. The mixture was then heated in an oil bath at 55° C. for two days. The reaction mixture was cooled and evaporated. To the white solid residue was added ether followed by filtration to provide the title compound.

Step 5: 5-[4-(2-Bromo-5-fluorophenoxy)piperidin-1-yl]pyrazine-2-carbonitrile To a suspension of 5-[4-(2-bromo-5-fluorophenoxy)piperidin-1-yl]pyrazine-2-carboxamide from Step 4 (1.65 g, 4.17 mmol) in TBF (50 mL) at 0° C. was added triethylamine (1.45 mL, 10.5 mmol) followed by trifluoroacetic anhydride (0.885 mL, 6.26 mmol). After a period of 10 min at 0° C., the reaction mixture was raised gradually to room temperature. The mixture was then partitioned between ethyl acetate and aqueous sodium bicarbonate. The organic phase was separated, dried over sodium sulfate and evaporated. The crude mixture was purified by flash chromatography (35% ethyl acetate in hexane) to provide the title compound.

Step 6: 2-[4-(2-Bromo-5-fluorophenoxy)piperidin-1-yl]-5-(2H-tetrazol-5-yl)pyrazine To a solution of 5-[4-(2-bromo-5-fluorophenoxy)piperidin-1-yl]pyrazine-2-carbonitrile from Step 5 (0.200 g, 0.530 mmol) in DMF (2 mL) was added sodium azide (0.070 g, 1.06 mmol) and ammonium chloride (0.284 g, 5.30 mmol). After a period of 3 h at 130° C., the reaction mixture was cooled and partitioned between ethyl acetate and brine. The organic phase was separated, dried over sodium sulfate and evaporated. To the crude product was added a mixture of ether-hexane (1:1). The resulting solid was filtered to provide the title compound.

Alternative Procedure for Step 6:

To a solution of 5-[4-(2-bromo-5-fluorophenoxy)piperidin-1-yl]pyrazine-2-carbonitrile from Step 5 (11.1 g, 29.4 mmol) in DMF (100 mL) was added sodium azide (3.83 g, 58.9 mmol) and ammonium chloride (1.73 g, 32.4 mmol). After a period of 4 h at 130° C., the reaction mixture was cooled and partitioned between ethyl acetate and 1 M HCl. The precipitate was filtered and washed with water and ether. The filtrate was filtered again and the solid washed with water and ether. The solids were combined and toluene was added. The toluene was evaporated under reduced pressure to provide the title compound.

Step 7: Ethyl (5-{5-[4-(2-bromo-5-fluorophenoxy) piperidin-1-yl]pyrazin-2-yl}-1H-tetrazol-1-yl)acetate (Isomer A) and Ethyl (5-{5-[4-(2-bromo-5-fluorophenoxy)piperidin-1-yl]pyrazin-2-yl}-2H-tetrazol-2-yl)acetate (Isomer B)

To a mixture of 2-[4-(2-bromo-5-fluorophenoxy)piperidin-1-yl]-5-(2H-tetrazol-5-yl)pyrazine from Step 6 (0.100 g, 0.238 mmol) in DMF (2 mL) was added sodium hydride (60% in oil) (0.015 g, 0.38 mmol) followed by ethyl bromoacetate (0.040 mL, 0.359 mmol). After a period of 2 h at 100° C., the reaction mixture was partitioned between ethyl acetate and 1 N HCl. The organic phase was separated, dried over sodium sulfate and evaporated. The crude mixture was separated by flash chromatography (30% to 50% ethyl acetate in hexane) to provide the more mobile the isomer A and the less mobile isomer B.

Isomer A: $^1$H NMR (400 MHz, acetone-$d_6$): δ 9.00 (s, 1H), 8.45 (s, 1H), 7.65 (m, 1H), 7.15 (dd, 1H), 6.75 (dt, 1H), 5.75 (s, 2H), 5.00 (m, 1H), 4.25 (q, 2H), 4.10-3.90 (m, 4H), 2.20 (m, 2H), 1.95 (m, 2H), 1.20 (t, 3H).

Isomer B: $^1$H NMR (400 MHz, acetone-$d_6$): δ 8.85 (s, 1H), 8.45 (s, 1H), 7.65 (m, 1H), 7.15 (dd, 1H), 6.75 (dt, 1H), 5.75 (s, 2H), 4.95 (m, 1H), 4.20 (q, 2H), 4.10-3.90 (m, 4H), 2.20 (m, 2H), 1.95 (m, 2H), 1.20 (t, 3H).

Alternative Procedure for Step 7B:

To a mixture of 2-[4-(2-bromo-5-fluorophenoxy)piperidin-1-yl]-5-(2H-tetrazol-5-yl)pyrazine from Step 6 (5.00 g, 11.9 mmol) and triethylamine (3.32 mL, 23.8 mmol) in THF (50 mL) at 60° C. was added tert-butyl bromoacetate (3.48 g, 17.9 mmol). After a period of 1 h at 60° C., the reaction mixture was partitioned between ethyl acetate and saturated ammonium chloride. The organic phase was separated, dried over sodium sulfate, filtered and evaporated. To the solid was added 50 mL of acetone followed by slow addition of 100 mL of hexane. The resulting solid was filtered to provide tert-butyl (5-{5-[4-(2-bromo-5-fluorophenoxy)piperidin-1-yl] pyrazin-2-yl}-2H-tetrazol-2-yl)acetate.

Step 8: (5-{5-[4-(2-Bromo-5-fluorophenoxy)piperidin-1-yl]pyrazin-2-yl}-1H-tetrazol-1-yl)-acetic acid To a solution of ethyl (5-{5-[4-(2-bromo-5-fluorophenoxy)piperidin-1-yl]pyrazin-2-yl}-1H-tetrazol-1-yl)acetate (Isomer A) from Step 7 (0.067 g, 0,132 mmol) in THF (2 mL) and MeOH (2 mL) was added 1 N NaOH (2 mL). After approximately 2 h, ethyl acetate and 1 N HCl were added to the reaction mixture. The organic phase was separated, dried over sodium sulfate and evaporated to give the title compound.

$^1$H NMR (400 MHz, acetone-$d_6$): δ 9.00 (s, 1H), 8.45 (s, 1H), 7.65 (m, 1H), 7.15 (dd, 1H), 6.75 (dt, 1H), 5.75 (s, 2H), 5.00 (m, 1H), 4.10-3.90 (m, 4H), 2.20 (m, 2H), 1.95 (m, 2H); MS (−ESI) 476 (M−1).

EXAMPLE 2

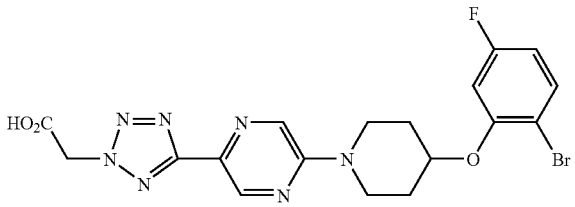

(5-{5-[4-(2-Bromo-5-fluorophenoxy)piperidin-1-yl]
pyrazin-2-yl}-2H-tetrazol-2-yl)acetic acid The title compound was obtained from ethyl (5-{5-[4-(2-bromo-5-fluorophenoxy)piperidin-1-yl]pyrazin-2-yl}-2H-tetrazol-2-yl)acetate (Isomer B) from Step 7 of Example 1 using the same conditions as described in Step 8 of Example 1.

$^1$H NMR (400 MHz, acetone-d$_6$): δ 8.85 (s, 1H), 8.55 (s, 1H), 7.65 (m, 1H), 7.15 (dd, 1H), 6.75 (dt, 1H), 5.75 (s, 2H), 4.95 (m, 1H), 4.10-3.90 (m, 4H), 2.20 (m, 2H), 1.95 (m, 2H); MS (+ESI) 478 (M+1).

Alternative Procedure:

tert-Butyl (5-{5-[4-(2-bromo-5-fluorophenoxy)piperidin-1-yl]pyrazin-2-yl}-2H-tetrazol-2-yl)acetate (2.50 g, 4.68 mmol) was dissolved in a mixture of TFA (11.3 mL) and water (1.3 mL). After a period of 18 h at room temperature the reaction mixture was evaporated followed by two co-evaporations with toluene. The yellow oil was dissolved in ethyl acetate (12.5 mL) and hexane (37.5 mL) was then added slowly. The resulting solid was filtered to provide (5-{5-[4-(2-bromo-5-fluorophenoxy)piperidin-1-yl]pyrazin-2-yl}-2H-tetrazol-2-yl)acetic acid.

EXAMPLE 3

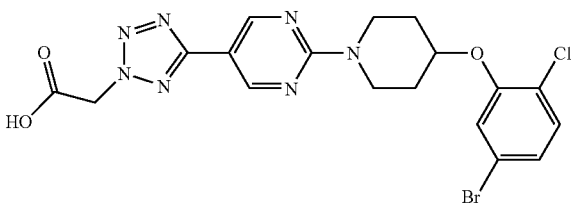

(5-{2-[4-(5-Bromo-2-chlorophenoxy)piperidin-1-yl]
pyrimidin-5-yl}-2H-tetrazol-2-yl)acetic acid Step 1: 1-(5-Bromopyrimidin-2-yl)piperidin-4-ol A mixture of 5-bromo-2-chloropyrimidine (5 g, 25.8 mmol), piperidin-4-ol (2.88 g, 28.4 mmol) and triethylamine (5.40 mL, 38.8 mmol) in EtOH (51.7 mL) was heated at 90° C. for 0.5 h. The solvent was evaporated, the residue was diluted with 1N HCl (20 mL) and extracted with EtOAc (3×15 mL). The combined organic fractions were dried over Na$_2$SO$_4$ and the solvent was evaporated. The product was recrystallized from CH$_2$Cl$_2$/hexanes, filtered and washed with hexanes to afford the title product.

$^1$H NMR (500 MHz, acetone-d$_6$): δ 8.36 (s, 2H), 4.29 (dt, 2H), 3.94-3.87 (m, 1H), 3.38 (ddd, 2H), 1.91-1.85 (m, 2H), 1.51-1.42 (m, 2H) ppm. MS: m/z 258, 260 (MH$^+$).

Step 2: 2-(4-Hydroxypiperidin-1-yl)pyrimidine-5-carbonitrile

A mixture of 1-(5-bromopyrimidin-2-yl)piperidin-4-ol (5 g, 19.37 mmol) and copper(I) cyanide (6.94 g, 77 mmol) in DMF (48.4 mL) was heated at 140° C. for 18 h. The mixture was diluted with water (100 mL) and EtOAc (50 mL) and filtered through celite. The filtrate was extracted with EtOAc (3×20 mL). The combined organic fractions were washed with 1N HCl (20 mL) then dried over Na$_2$SO$_4$. The solvent was evaporated and the product was recrystallized from CH$_2$Cl$_2$/hexanes, filtered and washed with hexanes to afford the title compound.

$^1$H NMR (500 MHz, acetone-d$_6$): δ 8.64 (s, 2H), 4.35 (dt, 2H), 3.98 (t, 1H), 3.60 (ddd, 2H), 1.95-1.89 (m, 2H), 1.57-1.48 (m, 2H). MS: m/z 205 MH$^+$).

Step 3: 1-[5-(1H-Tetrazol-5-yl)pyrimidin-2-yl]piperidin-4-ol

A mixture of 2-(4-hydroxypiperidin-1-yl)pyrimidine-5-carbonitrile (2 g, 9.79 mmol), sodium azide (0.955 g, 14.69 mmol) and ammonium chloride (1.048 g, 19.59 mmol) in DMF (24.48 mL) was heated at 130° C. for 1 h. The mixture was cooled to RT, diluted with 1N NaOH (5 mL), washed Et$_2$O (2×10) mL. The aqueous layer was acidified to pH about 1 with 2 N HCl and placed in the refrigerator for 1 h. The solid was filtered and washed with water followed by Et$_2$O. The solid was dried under high vacuum to afford the title compound.

$^1$H NMR (500 MHz, acetone-d$_6$): δ 8.98-8.93 (m, 2H), 4.43 (dt, 2H), 3.99-3.94 (m, 1H), 3.59-3.52 (m, 2H), 1.97-1.90 (m, 2H), 1.57-1.48 (m, 2H). MS: m/z 248 (MH$^+$).

Step 3: Ethyl {5-[2-(4-hydroxypiperidin-1-yl)pyrimidin-5-yl]-2H-tetrazol-2-yl}acetate A mixture of 1-[5-(1H-tetrazol-5-yl)pyrimidin-2-yl]piperidin-4-ol (550 mg, 2.224 mmol), triethylamine (0.62 mL, 4.45 mmol), ethyl bromoacetate (371 μL, 3.34 mmol) in THF (77.4 mL) was heated at 80° C. for 1 h. The solvent was evaporated, diluted with water (5 mL) and slurried with Et$_2$O (5 mL). The mixture was filtered and washed with water followed by Et$_2$O. The solid was dried under high vacuum to afford the title compound.

$^1$H NMR (500 MHz, acetone-d$_6$): δ 8.96 (s, 2H), 5.73 (s, 2H), 4.48-4.40 (m, 2H), 4.30 (q, 2H), 3.96 (d, 1H), 1.96-1.89 (m, 2H), 1.56-1.48 (m, 2H), 1.30 (t, 3H). MS: m/z 334 (MH$^+$).

Step 4: Ethyl (5-{2-[4-(5-bromo-2-chlorophenoxy)piperidin-1-yl]pyrimidin-5-yl}-2H-tetrazol-2-yl)acetate To a solution of ethyl {5-[2-(4-hydroxypiperidin-1-yl)pyrimidin-5-yl]-2H-tetrazol-2-yl}acetate (44 mg, 0.132 mmol), 5-bromo-2-chlorophenol (32.9 mg, 0.158 mmol) and triphenylphosphine (45 mg, 0.172 mmol) in THF (660 μL) was added diethyl azodicarboxylate (27.2 μL, 0.172 mmol). The mixture was heated at 50° C. for 4 h. The solvent was evaporated and the crude product was purified by Combiflash chromatography (SiO₂-12 g, gradient elution of 10-50% EtOAc/hexanes over 30 min) to afford the title product as a solid. MS: m/z 422, 424 (MH⁺).

Step 5: (5-{2-[4-(5-Bromo-2-chlorophenoxy)piperidin-1-yl]pyrimidin-5-yl}-2H-tetrazol-2-yl)acetic acid To a solution of the ethyl (5-{2-[4-(5-bromo-2-chlorophenoxy)piperidin-1-yl]pyrimidin-5-yl}-2H-tetrazol-2-yl)acetate (50 mg, 0.096 mmol) in THF (319 µL) and MeOH (159 µL) was added 2 N NaOH (96 µL, 0.191 mmol) and the was mixture stirred at RT for 10 min. The THF and MeOH were evaporated and the aqueous layer was washed with Et₂O (2×2 mL). The aqueous layer was acidified to pH 1 with 2 N HCl and stirred for 5 min. The mixture was filtered and washed with water followed by 1:1 Et₂O/hexanes. The solid was dried under high vacuum to afford the title compound.

¹H NMR (500 MHz, acetone-d₆): δ 9.00 (s, 2H), 7.49 (d, 1H), 7.40 (d, 1H), 7.18 (dd, 1H), 5.73 (s, 2H), 5.00-4.95 (m, 1H), 4.28-4.21 (m, 2H), 4.03-3.96 (m, 2H), 2.17-2.09 (m, 2H), 1.95-1.85 (m, 2H). MS: m/z 494, 496 (MH⁺).

EXAMPLE 4

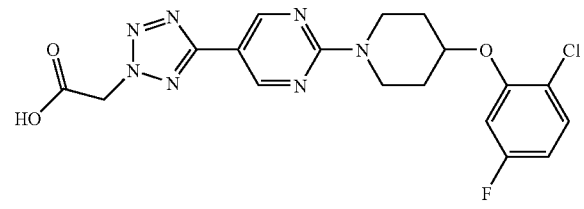

(5-{2-[4-(2-Chloro-5-fluorophenoxy)piperidin-1-yl]pyrimidin-5-yl}-2H-tetrazol-2-yl)acetic acid Step 1: Ethyl 5-{2-[4-(2-chloro-5-fluorophenoxy)piperidin-1-yl]pyrimidin-5-yl}-2H-tetrazol-2-yl)acetate The title compound was prepared in a similar manner as that described for Example 3 (step 4) from ethyl {5-[2-(4-hydroxypiperidin-1-yl)pyrimidin-5-yl]-2H-tetrazol-2-yl}acetate, 2-chloro-5-fluorophenol, triphenylphosphine and diethyl azodicarboxylate.

MS: m/z 462 (MH⁺).

Step 2: (5-{2-[4-(2-Chloro-5-fluorophenoxy)piperidin-1-yl]pyrimidin-5-yl}-2H-tetrazol-2-yl)acetic acid The title compound was prepared in a similar manner as that described for Example 3 (step 5) from ethyl 5-{2-[4-(2-chloro-5-fluorophenoxy)piperidin-1-yl]pyrimidin-5-yl}-2H-tetrazol-2-yl)acetate and aqueous NaOH.

¹H NMR (500 MHz, acetone-d₆): δ 9.00 (s, 2H), 7.46 (dd, 1H), 7.17 (dd, 1H), 6.80 (td, 1H), 5.74 (s, 2H), 4.96-4.91 (m, 1H), 4.27-4.20 (m, 2H), 4.03-3.96 (m, 2H), 2.16-2.09 (m, 2H), 1.93-1.85 (m, 2H). MS: m/z 434 (MH⁺).

EXAMPLE 5

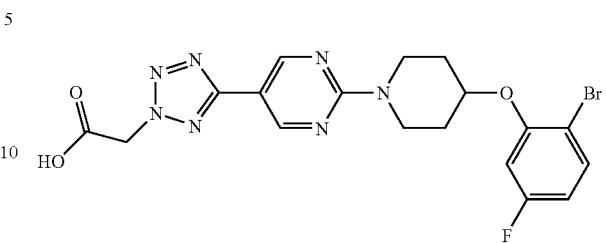

(5-{2-[4-(2-Bromo-5-fluorophenoxy)piperidin-1-yl]pyrimidin-5-yl}-2H-tetrazol-2-yl)acetic acid Step 1: Ethyl ((5-{2-[4-(2-bromo-5-fluorophenoxy)piperidin-1-yl]pyrimidin-5-yl}-2H-tetrazol-2-yl)acetate The title compound was prepared in a similar manner as that described for Example 3 (step 4) from ethyl {5-[2-(4-hydroxypiperidin-1-yl)pyrimidin-5-yl]-2H-tetrazol-2-yl}acetate, 2-bromo-5-fluorophenol, triphenylphosphine and di-tert-butyl azodicarboxylate.

¹H NMR (500 MHz, acetone-d₆): δ 9.01-8.97 (m, 2H), 7.63 (dd, 1H), 7.14 (dd, 1H), 6.76 (td, 1H), 5.74 (s, 2H), 4.99-4.94 (m, 1H), 4.30 (q, 2H), 4.22-4.15 (m, 2H), 4.11-4.04 (m, 2H), 2.11 (dd, 2H), 1.95-1.87 (m, 2H), 1.31 (t, 3H). MS: m/z 506, 508 (MH⁺).

Step 2: (5-{2-[4-(2-Bromo-5-fluorophenoxy)piperidin-1-yl]pyrimidin-5-yl}-2H-tetrazol-2-yl)acetic acid The title compound was prepared in a similar manner as that described for Example 3 (step 5) from ethyl ((5-{2-[4-(2-bromo-5-fluorophenoxy)piperidin-1-yl]pyrimidin-5-yl}-2H-tetrazol-2-yl)acetate and aqueous NaOH.

¹H NMR (500 MHz, acetone-d₆): δ 9.00 (s, 2H), 7.63 (t, 1H), 7.14 (d, 1H), 6.75 (d, 1H), 5.71 (s, 2H), 4.96 (s, 1H), 4.21-4.14 (m, 2H), 4.11-4.05 (m, 2H), 2.14-2.08 (m, 2H), 1.96-1.87 (m, 2H). MS: m/z 478,480 (MH⁺).

EXAMPLE 6

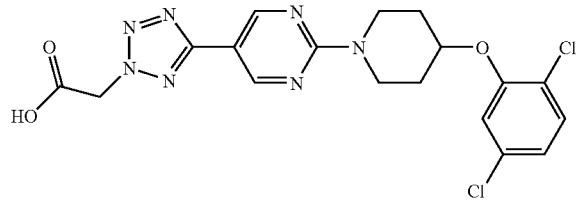

(5-{2-[4-(2,5-Dichlorophenoxy)piperidin-1-yl]pyrimidin-5-yl}-2H-tetrazol-2-yl)acetic acid Step 1: Ethyl (5-{2-[4-(2,5-dichlorophenoxy)piperidin-1-yl]pyrimidin-5-yl}-2H-tetrazol-2-yl)acetate The title compound was prepared in a similar manner as that described for Example 3 (step 4) from ethyl {5-[2-(4-hydroxypiperidin-1-yl)pyrimidin-5-yl]-2H-tetrazol-2-yl}acetate, 2,5-dichlorophenol, triphenylphosphine and di-tert-butyl azodicarboxylate.

MS: m/z 478, 480 (MH⁺).

Step 2: ((5-{2-[4-(2,5-Dichlorophenoxy)piperidin-1-yl]pyrimidin-5-yl}-2H-tetrazol-2-yl)acetic acid The title compound was prepared in a similar manner as that described for Example 3 (step 5) from ethyl (5-{2-[4-(2,5-dichlorophenoxy)piperidin-1-yl]pyrimidin-5-yl}-2H-tetrazol-2-yl)acetate and aqueous NaOH.

$^1$H NMR (500 MHz, acetone-$d_6$): δ 9.00 (s, 2H), 7.46 (d, 1H), 7.36 (s, 1H), 7.04 (d, 1H), 5.74 (s, 2H), 4.98 (s, 1H), 4.28-4.21 (m, 2H), 4.03-3.96 (m, 2H), 2.16-2.09 (m, 2H), 1.92-1.86 (m, 2H). MS: m/z 450, 452 (MH$^+$).

EXAMPLE 7

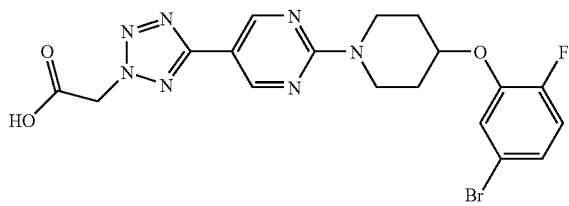

(5-{2-[4-(5-Bromo-2-fluorophenoxy)piperidin-1-yl]pyrimidin-5-yl}-2H-tetrazol-2-yl)acetic acid Step 1: Ethyl (5-{2-[4-(5-bromo-2-fluorophenoxy)piperidin-1-yl]pyrimidin-5-yl}-2H-tetrazol-2-yl)acetate The title compound was prepared in a similar manner as that described for Example 3 (step 4) from ethyl {5-[2-(4-hydroxypiperidin-1-yl)pyrimidin-5-yl]-2H-tetrazol-2-yl}acetate, 5-bromo-2-fluorophenol, triphenylphosphine and di-tert-butyl azodicarboxylate.

MS: m/z 506, 508 (MH$^+$).

Step 2: (5-{2-[4-(5-Bromo-2-fluorophenoxy)piperidin-1-yl]pyrimidin-5-yl}-2H-tetrazol-2-yl)acetic acid The title compound was prepared in a similar manner as that described for Example 3 (step 5) from ethyl (5-{2-[4-(5-bromo-2-fluorophenoxy)piperidin-1-yl]pyrimidin-5-yl}-2H-tetrazol-2-yl)acetate and aqueous NaOH.

$^1$H NMR (500 MHz, acetone-$d_6$): δ 8.99 (s, 2H), 7.49 (d, 1H), 7.17 (d, 2H), 5.72 (s, 2H), 4.92-4.83 (m, 1H), 4.41-4.33 (m, 2H), 4.87-4.79 (m, 2H), 2.18-2.11 (m, 2H), 1.88-1.78 (m, 2H). MS: m/z 478, 480 (MH$^+$).

EXAMPLE 8

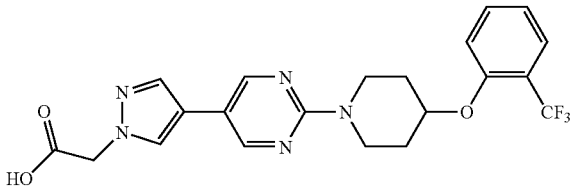

Step 1: 5-Bromo-2-{4-[2-(trifluoromethyl)phenoxy]piperidin-1-yl}pyrimidine

Into a 100-mL flask equipped with a magnetic stirbar was added 5-bromo-2-chloropyrimidine (3.80 g, 19.5 mmol), 4-[2-(trifluoromethyl)phenoxy]piperidine hydrochloride (6.90 g, 24.5 mmol) and 2-propanol (25 mL). The suspension was treated with N,N-diisopropylethylamine (8.6 mL, 49 mmol) and stirred at room temperature for 10 min and then heated to 100° C. for 16 h. After this time, the mixture was cooled to room temperature, poured into a 250-mL separatory funnel containing saturated aqueous NH$_4$Cl (125 mL) and the mixture was extracted with ethyl acetate (3×50 mL). The combined organic layers were washed with brine, dried over MgSO$_4$, filtered and the solvent was evaporated under reduced pressure. The crude solid was triturated in diethyl ether to yield the title compound as an off-white solid. MS (ESI, Q$^+$) m/z 403, 405 (M+1 for $^{35}$Br and $^{37}$Br).

Step 2: 5-(4,4,5,5-Tetramethyl-1,3,2-dioxaborolan-2-yl)-2-{4-[2-(trifluoromethyl)phenoxy]piperidin-1-yl}pyrimidine Into a flame-dried 250-mL round-bottom flask equipped with a magnetic stirbar and under nitrogen was added bis(pinacolato)diboron (1.89 g, 7.5 mmol), 5-bromo-2-{4-[2-(trifluoromethyl)phenoxy]piperidin-1-yl}pyrimidine (2.0 g, 5.0 mmol), PdCl$_2$(dppf) (0.20 g, 0.25 mmol) and potassium acetate (1.95 g, 20.0 mmol). The flask containing the solids was evacuated under vacuum and backfilled with nitrogen (repeated 3 times). DMF (50 mL) was added to the flask and the suspension degassed with nitrogen for 20 min, before being heating to 85° C. for 1 h. The dark black reaction mixture was cooled to room temperature, and the DMF was removed under rotary evaporation under reduced pressure. The solids were suspended in a 1:1 mixture of diethyl ether/ethyl acetate. The mixture was cooled, poured into a 250 mL separatory funnel containing water (150 mL) and the mixture was extracted. The combined organic layers were washed with brine and dried over MgSO$_4$. The solution was filtered through a short plug of silica gel, washing with 1:1 diethyl ether: ethyl acetate and the solvent was evaporated under reduced pressure. The crude solid was resuspended in heptanes (50 mL), and sonicated for 5 min. The suspension was filtered through a plug of celite on a sintered glass funnel. The resulting filtrate was cooled to −78° C. for 15 min. The resulting suspension was filtered through Whatman #1 filter paper on a Hirsch funnel, washing with cold hexanes and the resulting light brown solid was collected. MS (ESI, Q$^+$) m/z 450 (M+1).

Step 3: Ethyl [4-(2-{4-[2-(trifluoromethyl)phenoxy]piperidin-1-yl}pyrimidin-5-yl)-1H-pyrazol-1-yl]acetate Into a 50-mL round-bottom flask equipped with a magnetic stirbar and reflux condenser was added 5-(4,4,5,5-tetramethyl-1,3,2-dioxaborolan-2-yl)-2-{4-[2-(trifluoromethyl)phenoxy]piperidin-1-yl}pyrimidine (311 mg, 1.35 mmol), ethyl (4-bromo-1H-pyrazol-1-yl)acetate (400 mg, 0.89 mmol), PdCl$_2$(dppf) (36 mg, 0.05 mmol), 2 M aqueous sodium carbonate solution (0.89 mL, 1.8 mmol) and DMF (4 mL). The resulting suspension was degassed under nitrogen for 20 min and then heated in the microwave to 120° C. for 20 min. The mixture was poured into a 125-mL separatory funnel containing a saturated aqueous KH$_2$PO$_4$ solution (50 mL) and the mixture was extracted with ethyl acetate (3×30 mL).

The combined organic layers were washed with brine, dried over MgSO$_4$, filtered and the solvent was evaporated under reduced pressure. Purification by column chromatography through silica gel, eluting with 30% EtOAc in hexanes to 70% EtOAc in hexanes as a gradient gave the title compound as a white solid. MS (ESI, Q$^+$) m/z 476 (M+1).

Step 4: [4-(2-{4-[2-(trifluoromethyl)phenoxy]piperidin-1-yl}pyrimidin-5-yl)-1H-pyrazol-1-yl]acetic acid Into a 10-mL flask equipped with a magnetic stirbar was added ethyl [4-(2-{4-[2-(trifluoromethyl)phenoxy]piperidin-1-yl}pyrimidin-5-yl)-1H-pyrazol-1-yl]acetate-(50 mg, 0.10 mmol), methanol (2 mL) and 1 M aqueous sodium hydroxide solution (0.52 mL, 0.53 mmol). The suspension was heated to 80° C. for 2 h. The reaction mixture was concentrated to remove the methanol and the residue was poured into a 125-mL separatory funnel containing saturated aqueous KH$_2$PO$_4$ solution (75 mL) and the mixture was extracted with ethyl acetate (3×30 mL). The combined organic layers were washed with brine, dried over MgSO$_4$, filtered and the solvent was evaporated under reduced pressure to give the desired product.

$^1$H NMR (400 MHz, d$_4$-MeOH): δ 8.55 (s, 2H), 8.00 (s, 1H), 7.84 (s, 1H), 7.61-7.55 (m, 2H), 7.25 (d, J=8.5 Hz, 1H), 7.06 (t, J=7.5 Hz, 1H), 5.02 (s, 2H), 4.89-4.86 (m, 1H), 4.03-3.91 (m, 4H), 2.06-2.00 (m, 2H), 1.90-1.84 (m, 2H); MS (ESI, Q$^+$) m/z 448 (M+1).

EXAMPLE 9

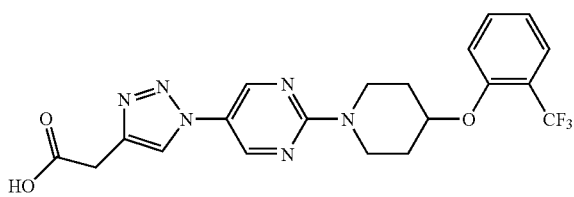

Step 1: 2-[1-(2-{4-[2-(Trifluoromethyl)phenoxy]piperidin-1-yl}pyrimidin-5-yl)-1H-1,2,3-triazol-4-yl]ethanol Into a 5-mL vial equipped with a magnetic stirbar was added 4-[2-(trifluoromethyl)phenoxy]piperidine hydrochloride (100 mg, 0.25 mmol), copper(I) iodide (48 mg, 0.25 mmol), sodium azide (33 mg, 0.5 mmol) and racemic trans-N,N'-dimethylcyclohexane-1,2-diamine (53 mg, 0.37 mmol). The solids were taken up in ethanol (1.4 mL) and water (0.6 mL) and the sealed flask was then heated to 75° C. in an oil bath for 5 min. A solution of sodium L-ascorbate (49 mg, 0.25 mmol) dissolved in 1 mL of EtOH:water (7:3) and added dropwise to the suspension over 2 h with heating. The reaction mixture was cooled to room temperature, diluted with ethyl acetate (25 mL) and filtered through a pad of silica gel on a sintered glass funnel, washing with ethyl acetate. The resulting filtrate was concentrated and used directly in the next reaction.

Into a 50-mL flask equipped with a magnetic stirbar was added the crude reaction mixture from above (91 mg, 0.25 mmol), sodium ascorbate (3 mg, 0.01 mmol), copper(I) iodide (3 mg, 0.01 mmol), ethanol (3.5 mL) and water (1.5 mL). The suspension was treated with 3-butyn-1-ol (52 mg, 0.75 mmol) and stirred at room temperature for 2 h. The reaction mixture was concentrated to remove the ethanol. The mixture was poured into a 125-mL separatory funnel containing water (75 mL) and the mixture was extracted with ethyl acetate (3×25 mL). The combined organic layers were washed with brine, dried over MgSO$_4$, filtered and the solvent was evaporated under reduced pressure. Purification by column chromatography through silica gel, eluting with 75% EtOAc in hexanes to 100% EtOAc in hexanes as a gradient gave the desired product as a yellow solid. MS (ESI, Q$^+$) m/z 435 (M+1).

Step 2: [1-(2-{4-[2-(Trifluoromethyl)phenoxy]piperidin-1-yl}pyrimidin-5-yl)-1H-1,2,3-triazol-4-yl]acetaldehyde Into a 25-mL flask equipped with a magnetic stirbar was added 2-[1-(2-{4-[2-(trifluoromethyl)phenoxy]piperidin-1-yl}pyrimidin-5-yl)-1H-1,2,3-triazol-4-yl]ethanol (50 mg, 0.12 mmol) and dichloromethane (5 mL). To the solution was added Dess-Martin periodinane (59 mg, 0.14 mmol) and the reaction mixture stirred at room temperature for 1 h. The reaction mixture was concentrated and purified by column chromatography through silica gel, eluting with 60:40 Hexanes/EtOAc to 40:60 Hexanes/EtOAc, yielding the desired product as a yellow solid. MS (ESI, Q$^+$) m/z 433 (M+1).

Step 3: [1-(2-{4-[2-(Trifluoromethyl)phenoxy]piperidin-1-yl}pyrimidin-5-yl)-1H-1,2,3-triazol-4-yl]acetic acid Into a 10-mL round-bottom flask equipped with a magnetic stirbar was added sodium chlorite (28 mg, 0.31 mmol), 2-methyl-2-butene (32 μL, 0.31 mmol) and sodium dihydrogen phosphate (37 mg, 0.31 mmol) in water (1.0 mL). To this solution was added [1-(2-{4-[2-(trifluoromethyl)phenoxy]piperidin-1-yl}pyrimidin-5-yl)-1H-1,2,3-triazol-4-yl]acetaldehyde (22 mg, 0.05 mmol) dissolved in acetone (1.0 mL). The reaction was stirred at room temperature for 1 h. The reaction was concentrated, poured into a 50-mL separatory funnel containing saturated aqueous KH$_2$PO$_4$ solution (30 mL) and the mixture was extracted with ethyl acetate (3×10 mL). The combined organic layers were washed with brine, dried over magnesium sulfate, filtered and the solvent was evaporated under reduced pressure to give the desired product.

$^1$H NMR (400 MHz, d$_4$-MeOH) δ 8.73 (s, 2H), 8.33 (s, 1H), 7.61-7.56 (m, 2H), 7.27 (d, J=8.5 Hz, 1H), 7.07 (t, J=7.5 Hz, 1H), 4.93-4.90 (m, 1H), 4.12-4.02 (m, 4H), 3.87 (s, 2H), 2.08-2.02 (m, 2H), 1.94-1.88 (m, 2H); MS (ESI, Q$^+$) m/z 449 (M+1).

EXAMPLE 10

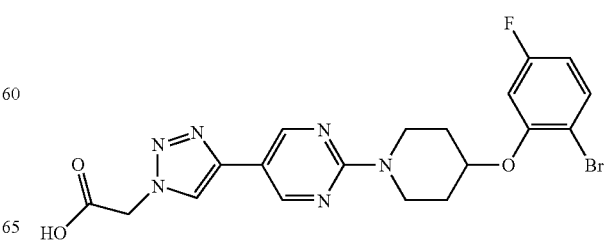

Step 1: 5-Bromo-2-[4-(2-bromo-5-fluorophenoxy) piperidin-1-yl]pyrimidine

Into a 100-mL sealable pressure flask equipped with a magnetic stirbar was added 5-bromo-2-chloropyrimidine (2.50 g, 12.9 mmol), 4-(2-bromo-5-fluorophenoxy)piperidine hydrochloride (4.00 g, 12.9 mmol), 2-propanol (30 mL) and N,N-diisopropylethylamine (4.50 mL, 25.8 mmol). The vial was sealed and heated to 120° C. for 3 h. The reaction mixture was cooled and poured into a 500 mL separatory funnel containing water (250 mL) and the mixture was extracted with ethyl acetate (3×75 mL). The combined organic layers were washed with brine, dried over $MgSO_4$, filtered and the solvent was evaporated under reduced pressure. The resulting oil was recrystallized from diethyl ether/hexanes and cooled to −40° C. to cause precipitation, then filtered through Whatman#1 filter paper to give a beige solid, which was dried overnight on the vacuum pump. MS (ESI, $Q^+$) m/z 432, 434, 437 (M+1 for $2\times^{35}Br$ and $^{37}Br$).

Step 2: 4-{2-[4-(2-Bromo-5-fluorophenoxy)piperidin-1-yl]pyrimidin-5-yl}-2-methylbut-3-yn-2-ol Into a flame-dried 25-mL sealable pressure flask equipped with a magnetic stirbar and under nitrogen was added 5-bromo-2-[4-(2-bromo-5-fluorophenoxy)piperidin-1-yl]pyrimidine (500 mg, 1.16 mmol), copper(I) iodide (44 mg, 0.23 mmol), $Pd(PPh_3)_4$ (100 mg, 0.09 mmol) and potassium carbonate (400 mg, 2.90 mmol). The flask was evacuated under vacuum (1 mm Hg) and backfilled with nitrogen (repeated 3 times). The solids were taken up in dimethoxyethane (4 mL) and water (4 mL) and degassed for 10 min with a stream of nitrogen. The contents of the flask where then heated to 90° C. and 2-methyl-3-butyn-2-ol (0.135 mL, 1.39 mmol) was added and the mixture heated at 90° C. for 1 h. The mixture was cooled, poured into a 250-mL separatory funnel containing water (125 mL) and the mixture was extracted with ethyl acetate (3×50 mL). The combined organic layers were washed with brine, dried over $MgSO_4$, filtered and the solvent was evaporated under reduced pressure. Purification by column chromatography through silica gel, eluting with 10% EtOAc in hexanes to 50% EtOAc in hexanes as a gradient gave the desired product as a beige solid.

MS (ESI, $Q^+$) m/z 434, 436 (M+1 for $^{35}Br$ and $^{37}Br$).

Step 3: 2-[4-(2-Bromo-5-fluorophenoxy)piperidin-1-yl]-5-ethynylpyrimidine

Into a 50-mL round-bottom flask equipped with a magnetic stirbar was added 4-{2-[4-(2-Bromo 5-fluorophenoxy)piperidin-1-yl]pyrimidin-5-yl}-2-methylbut-3-yn-2-ol (300 mg, 0.69 mmol) and toluene (10 mL). The reaction mixture was treated with sodium hydride (3 mg, 0.07 mmol, 60 wt % in mineral oil) and the contents of the flask heated to 110° C. without attaching a reflux condenser in order to remove the acetone formed during the deprotection stage. After 2.5 h, complete conversion of starting material was observed by TLC analysis. The reaction mixture was cooled to room temperature and then quenched with dropwise addition of a saturated aqueous $NH_4Cl$ solution (10 mL). The mixture was poured into a 125-mL separatory funnel containing water (50 mL) and the mixture was extracted with ethyl acetate (3×30 mL). The combined organic layers were washed with brine, dried over $MgSO_4$, filtered and the solvent was evaporated under reduced pressure. Purification by column chromatography through silica gel, eluting with 0% EtOAc in hexanes to 20% EtOAc in hexanes as a gradient gave the desired product as a clear oil.

MS (ESI, $Q^+$) m/z 376, 378 (M+1 for $^{35}Br$ and $^{37}Br$).

Step 4: Ethyl (4-{2-[4-(2-bromo-5-fluorophenoxy) piperidin-1-yl]pyrimidin-5-yl}-1H-1,2,3,3-triazol-1-yl)acetate Into a 25-mL round-bottom flask equipped with a magnetic stirbar was added 2-[4-(2-bromo-5-fluorophenoxy)piperidin-1-yl]-5-ethynylpyrimidine (160 mg, 0.43 mmol), isopropanol (2 mL), water (2 mL), copper(II) sulfate (7 mg, 0.04 mmol) and sodium ascorbate (17 mg, 0.09 mmol). The resulting suspension was treated with dropwise addition of azidoacetic acid ethyl ester (320 mg, 0.85 mmol) and stirred at room temperature for 16 h overnight. The mixture was poured into a 125 mL separatory funnel containing water (75 mL) and the mixture was extracted with ethyl acetate (3×50 mL). The combined organic layers were washed with brine, dried over $MgSO_4$, filtered and the solvent was evaporated under reduced pressure. Purification by column chromatography through silica gel, eluting with 20% EtOAc in hexanes to 60% EtOAc in hexanes as a gradient gave the desired product as a white solid.

MS (ESI, $Q^+$) m/z 505, 507 (M+1 for $^{35}Br$ and $^{37}Br$).

Step 5: (4-{2-[4-(2-Bromo-5-fluorophenoxy)piperidin-1-yl]pyrimidin-5-yl}-1H-1,2,3,3-triazol-1-yl) acetic acid To a solution of ethyl (4-{2-[4-(2-bromo-5-fluorophenoxy)piperidin-1-yl]pyrimidin-5-yl}-1H-1,2,3,3-triazol-1-yl)acetate (125 mg, 0.25 mmol) in tetrahydrofuran (2 mL) was added 1 N aqueous lithium hydroxide solution (1.3 mL, 1.25 mmol) and the suspension was heated to reflux for 1 h. The cooled reaction mixture was poured into a 125-mL separatory funnel containing saturated aqueous $KH_2PO_4$ solution (75 mL) and extracted with ethyl acetate (3×30 mL). The combined organic layers were washed with brine, dried over $MgSO_4$, filtered and concentrated to a solid. The solid was triturated in hot diethyl ether/ethyl acetate (1:1, 3 mL) and filtered to give a white solid.

$^1$H NMR (400 MHz, $d_6$-acetone) δ 8.85 (s, 2H), 8.41 (s, 1H), 7.64-7.61 (m, 1H), 7.25-7.21 (m, 11H), 6.80-6.75 (m, 1H), 5.06 (s, 2H), 4.94-4.92 (m, 1H), 4.15-4.09 (m, 2H), 3.94-3.89 (m, 2H), 2.06-2.02 (m, 2H), 1.84-1.78 (m, 2H). MS (ESI, $Q^+$) m/z 477, 479 (M+1 for $^{35}Br$ and $^{37}Br$).

EXAMPLE 11

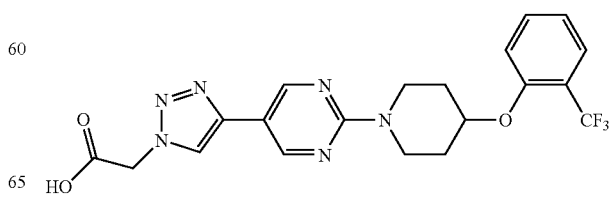

[4-(2-{4-[2-(Trifluoromethyl)phenoxy]piperidin-1-yl}pyrimidin-5-yl)-1H-1,2,3-triazol-1-yl]acetic acid MS (ESI, Q+) m/z 449 (M+1).

EXAMPLE 12

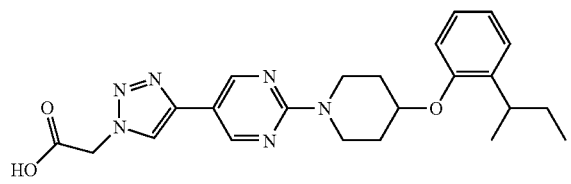

(4-{2-[4-(2-Butylphenoxy)piperidin-1-yl]pyrimidin-5-yl}-1H-1,2,3-triazol-1-yl)acetic acid MS (ESI, Q+) m/z 437 (M+1).

EXAMPLE 13

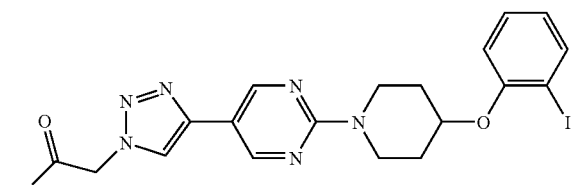

(4-{2-[4-(2-Iodophenoxy)piperidin-1-yl]pyrimidin-5-yl}-1H-1,2,3-triazol-1-yl)acetic acid MS (ESI, Q+) m/z 507 (M+1).

EXAMPLE 14

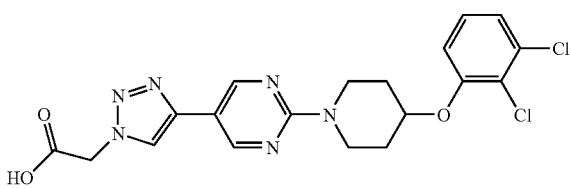

(4-{2-[4-(2,3-Dichlorophenoxy)piperidin-1-yl]pyrimidin-5-yl}-1H-1,2,3-triazol-1-yl)acetic acid MS (ESI, Q+) m/z 449 (M+1).

EXAMPLE 15

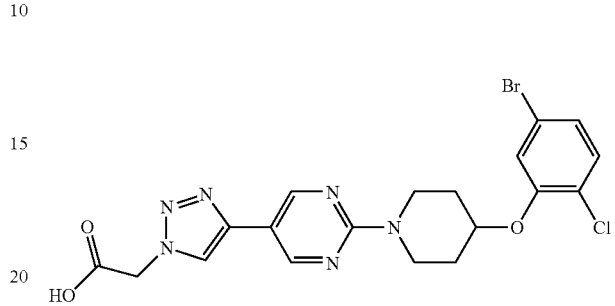

(4-{2-[4-(5-Bromo-2-chlorophenoxy)piperidin-1-yl]pyrimidin-5-yl}-1H-1,2,3-triazol-1-yl)acetic acid MS (−APCI, Q−) m/z 491, 493 (M−1 for $^{35}$Br and $^{37}$Br).

EXAMPLE 16

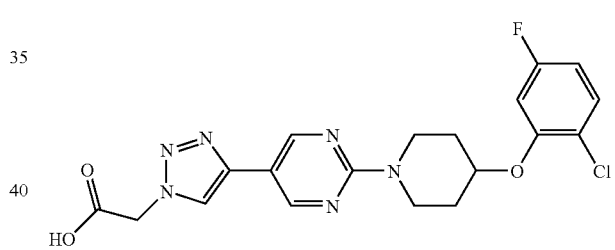

(4-{2-[4-(5-Fluoro-2-chlorophenoxy)piperidin-1-yl]pyrimidin-5-yl}-1H-1,2,3-triazol-1-yl)acetic acid MS (+APCI, Q+) m/z 433, 435 (M+1).

EXAMPLE 17

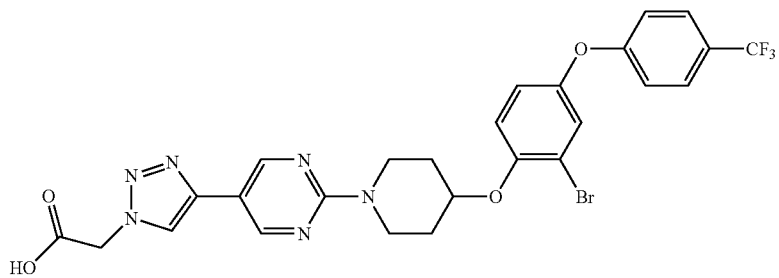

{4-[2-(4-{2-Bromo-4-[4-(trifluoromethyl)phenoxy]phenoxy}piperidin-1-yl)pyrimidin-5-yl]-1H-1,2,3-triazol-1-yl)acetic acid MS (APCI, Q+) m/z 619, 621 (M+1 for $^{35}$Br and $^{37}$Br).

EXAMPLE 18

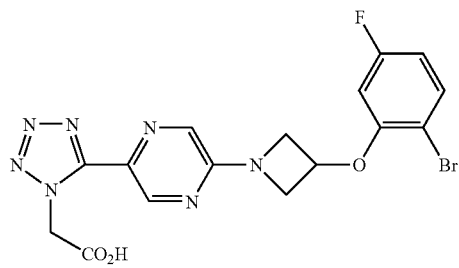

(5-{5-[3-(2-Bromo-5-fluorophenoxy)azetidin-1-yl]pyrazin-2-yl}-1H-tetrazol-1-yl)acetic acid Step 1: tert-Butyl 3-(2-bromo-5-fluorophenoxy)azetidine-1-carboxylate To a solution of Boc-3-hydroxyazetidine (1.50 g, 8.67 mmol) in DMF (9.1 mL) was added 1 M potassium tert-butoxide in THF (9.96 mL, 9.96 mmol) followed by 1-bromo-2,4-difluorobenzene (2.50 g, 13.0 mmol). After a period of 1 h at 50° C., the reaction mixture was partitioned between ethyl acetate and saturated ammonium chloride. The organic phase was separated, dried over sodium sulfate, filtered and evaporated under reduced pressure. The residue was purified by flash chromatography (15% ethyl acetate in hexane) to provide the title compound as a white solid.

Step 2: 3-(2-Bromo-5-fluorophenoxy)azetidine hydrochloride salt

To tert-butyl 3-(2-bromo-5-fluorophenoxy)azetidine-1-carboxylate (2.28 g, 6.59 mmol) in dioxane (40 mL) was added 4 M HCl in dioxane (4.49 mL, 19.8 mmol). After a period of 18 h, the white solid was filtered and washed with cold dioxane to give the title compound.

Step 3: Methyl 5-[3-(2-bromo-5-fluorophenoxy)azetidin-1-yl]pyrazine-2-carboxylate To a mixture of methyl 5-chloropyrazine-2-carboxylate (0.47 g, 2.7 mmol), 3-(2-bromo-5-fluorophenoxy)azetidine hydrochloride salt (0.80 g, 3.2 mmol) and potassium carbonate (0.75 g, 5.42 mmol) in dioxane (13 mL) was heated at 100° C. After a period of 4 h, the reaction mixture was partitioned between ethyl acetate and saturated ammonium chloride. The organic phase was separated, dried over sodium sulfate, filtered and evaporated under reduced pressure. The resulting solid was taken in ether and filtered to give the title compound.

Step 4: 5-[3-(2-Bromo-5-fluorophenoxy)azetidin-1-yl]pyrazine-2-carboxamide

To methyl 5-[3-(2-bromo-5-fluorophenoxy)azetidin-1-yl]pyrazine-2-carboxylate (0.080 g, 2.1 mmol) in MeOH was bubbled ammonia and the mixture was heated at 50° C. After 2 d, the methanol was evaporated followed by the addition of ether. The solid was filtered to provide the title compound as a white solid.

Step 5: 5-[3-(2-Bromo-5-fluorophenoxy)azetidin-1-yl]pyrazine-2-carbonitrile

To 5-[3-(2-bromo-5-fluorophenoxy)azetidin-1-yl]pyrazine-2-carboxamide (0.66 g, 1.8 mmol) in THF (30 mL) at 0° C. was added triethylamine (0.46 g, 4.5 mmol) followed by TFAA (0.57 g, 2.7 mmol). After 15 min at room temperature, the reaction mixture was partitioned between ethyl acetate and saturated sodium bicarbonate. The organic phase was separated, dried over sodium sulfate and filtered. The residue was purified by flash chromatography to provide the title compound as a white solid.

Step 6: 2-[3-(2-Bromo-5-fluorophenoxy)azetidin-1-yl]-5-(1H-tetrazol-5-yl)pyrazine A mixture of 5-[3-(2-bromo-5-fluorophenoxy)azetidin-1-yl]pyrazine-2-carbonitrile (0.48 g, 1.36 mmol), sodium azide (0.18 g, 2.7 mmol), and ammonium chloride (0.73 g, 1.36 mmol) in DMF (4 mL) was heated at 130° C. After a period of 4 h, the reaction mixture was partitioned between ethyl acetate and saturated ammonium chloride. The resulting solid was filtered and washed with water and ether. The solid was taken up in toluene and the solvent evaporated to provide the desired product.

Step 7: Ethyl (5-{5-[3-(2-bromo-5-fluorophenoxy)azetidin-1-yl]pyrazin-2-yl}-1H-tetrazol-1-yl)acetate (Isomer A) and ethyl (5-{5-[3-(2-bromo-5-fluorophenoxy)azetidin-1-yl]pyrazin-2-yl}-2H-tetrazol-2-yl)acetic acid (Isomer B)

The title compounds were prepared from 2-[3-(2-bromo-5-fluorophenoxy)azetidin-1-yl]-5-(1H-tetrazol-5-yl)pyrazine as described in Example 1, step 7.

Isomer A: $^1$H NMR (400 MHz, acetone-d$_6$): δ 8.99 (s, 1H), 8.10 (s, 1H), 7.65 (m, 1H), 6.95 (dd, 1H), 6.85 (dt, 1H), 5.75 (s, 2H), 5.50 (m, 1H), 4.85 (m, 2H), 4.30 (m, 2H), 4.20 (q, 2H), 1.20 (t, 3H).

Isomer B: $^1$H NMR (400 MHz, acetone-d$_6$): δ 8.85 (s, 1H), 8.10 (s, 1H), 7.65 (m, 1H), 6.95 (dd, 1H), 6.80 (dt, 1H), 5.70 (s, 2H), 5.45 (m, 1H), 4.80 (m, 2H), 4.20-4.30 (m, 4H), 1.20 (t, 3H).

Step 8: (5-{5-[3-(2-Bromo-5-fluorophenoxy)azetidin-1-yl]pyrazin-2-yl}-1H-tetrazol-1-yl)acetic acid The title compound was prepared as described in Example 1, step 8 from ethyl (5-{5-[3-(2-bromo-5-fluorophenoxy)azetidin-1-yl]pyrazin-2-yl}-1H-tetrazol-1-yl)acetate (Isomer A).

$^1$H NMR (400 MHz, acetone-d$_6$): δ 8.90 (s, 1H), 8.15 (s, 1H), 7.70 (m, 1H), 6.95 (dd, 1H), 6.85 (dt, 1H), 5.50 (s, 2H), 5.40 (m, 1H), 4.80 (m, 2H), 4.30 (m, 2H).

EXAMPLE 19

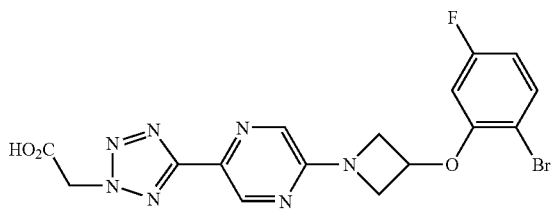

(5-{5-[3-(2-Bromo-5-fluorophenoxy)azetidin-1-yl]
pyrazin-2-yl}-2H-tetrazol-2-yl)acetic acid The title compound was prepared from ethyl (5-{5-[3-(2-bromo-5-fluorophenoxy)azetidin-1-yl]pyrazin-2-yl}-2H-tetrazol-2-yl)acetic acid (Isomer B) from Example 3, step 7 using conditions described in Example 1, step 8.

$^1$H NMR (400 MHz, acetone-$d_6$): δ 8.85 (s, 1H), 8.15 (s, 1H), 7.70 (m, 1H), 6.95 (dd, 1H), 6.85 (dt, 1H), 5.45 (m, 1H), 5.40 (s, 2H), 4.80 (m, 2H), 4.30 (m, 2H); MS (−ESI) 450 (M+1).

EXAMPLE 20

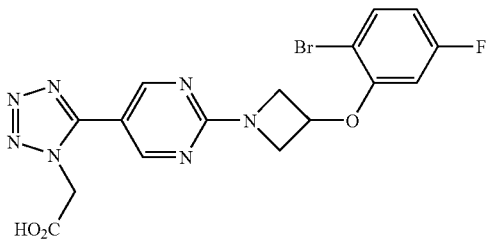

(5-{2-[3-(2-Bromo-5-fluorophenoxy)azetidin-1-yl]
pyrimidin-5-yl}-1H-tetrazol-1-yl)acetic acid The title compound was prepared in a similar manner as that described for Example 1 where 4-(2-bromo-5-fluorophenoxy)piperidine in step 3 was replaced by 3-(2-bromo-5-fluorophenoxy)azetidine and methyl 5-chloropyrazine-2-carboxylate was replaced with methyl 2-(methoxysulfonyl)pyrimidine-5-carboxylate.

MS (APCI, Q−) m/z 448, 450 (M−1 for $^{35}$Br and $^{37}$Br).

EXAMPLE 21

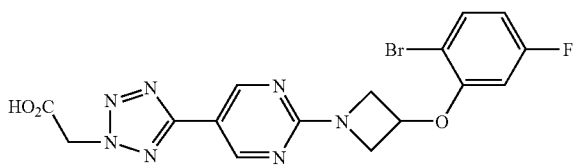

(5-{2-[3-(2-Bromo-5-fluorophenoxy)azetidin-1-yl]
pyrimidin-5-yl}-2H-tetrazol-2-yl)acetic acid The title compound was prepared in a similar manner as that described for Example 2 where 4-(2-bromo-5-fluorophenoxy)piperidine in step 3 was replaced by 3-(2-bromo-5-fluorophenoxy)azetidine and methyl 5-chloropyrazine-2-carboxylate was replaced with methyl 2-(methoxysulfonyl)pyrimidine-5-carboxylate.

MS (APCI, Q+) m/z 450, 452 (M+1 for $^{35}$Br and $^{37}$Br).

EXAMPLE 22

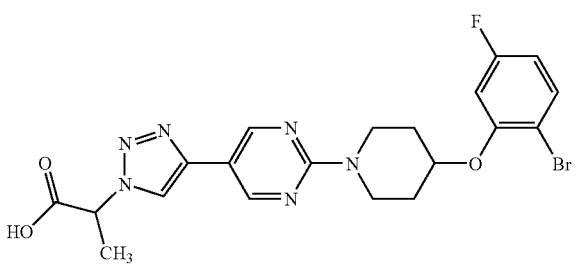

2-(4-{2-[4-(2-Bromo-5-fluorophenoxy)piperidin-1-yl]pyrimidin-5-yl}-1H-1,2,3-triazol-1-yl)propanoic acid Step 1: Ethyl 2-(4-{2-[4-(2-bromo-5-fluorophenoxy)
piperidin-1-yl]pyrimidin-5-yl}-1H-1,2,3-triazol-1-yl)
propanate The title compound was prepared in a similar manner as that described for Example 10, step 4. Into a 25-mL round-bottom flask equipped with a magnetic stirbar was added 2-[4-(2-bromo-5-fluorophenoxy)piperidin-1-yl]-5-ethynylpyrimidine (130 mg, 0.35 mmol), sodium azide (23 mg, 0.35 mmol) tert-butanol (1.5 mL), water (0.7 mL), copper(I) iodide (4 mg, 0.02 mmol) and sodium ascorbate (9 mg, 0.04 mmol). The resulting suspension was treated with dropwise addition of ethyl 2-bromopropionate (45 μL, 0.35 mmol) and stirred at room temperature for 16 h overnight. The mixture was poured into a 125 mL separatory funnel containing water (75 mL) and the mixture was extracted with ethyl acetate (3×50 mL). The combined organic layers were washed with brine, dried over MgSO$_4$, filtered and the solvent was evaporated under reduced pressure. Purification by column chromatography through silica gel, eluting with 5% EtOAc in hexanes to 55% EtOAc in hexanes as a gradient gave the desired product as a beige solid.

MS (ESI, Q$^+$) m/z 519, 521 (M+1 for $^{35}$Br and $^{37}$Br).

Step 2: 2-(4-{2-[4-(2-Bromo-5-fluorophenoxy)piperidin-1-yl]pyrimidin-5-yl}-1H-1,2,3-triazol-1-yl)
propanoic acid Into a 25 mL round-bottom flask equipped with a magnetic stirbar was added ethyl 2-(4-{2-[4-(2-bromo-5-fluorophenoxy)piperidin-1-yl]pyrimidin-5-yl}-1H-1,2,3-triazol-1-yl) propanate (55 mg, 0.11 mmol), 1 mL of THF and 0.5 mL of MeOH. A 1.0 M lithium hydroxide solution in water (0.53 mL, 0.53 mmol) was added and the reaction mixture was stirred at room temperature for 2 h. The mixture was poured into a 125 mL separatory funnel containing saturated aqueous KH$_2$PO$_4$ solution (75 mL) and the mixture was extracted with ethyl acetate (3×50 mL). The combined organic layers were washed with brine, dried over MgSO$_4$, filtered and the solvent was evaporated under reduced pressure to yield a beige crystalline solid.

$^1$H NMR (400 MHz, acetone-d$_6$): δ 8.80 (s, 2H), 8.41 (s, 1H), 7.56 (dd, 1H), 7.06 (dd, 1H), 6.73-6.64 (td, 1H), 5.58 (q, 1H), 4.90-4.83 (m, 1H), 4.15-4.08 (m, 2H), 3.96-3.89 (m, 2H), 2.04-2.00 (m, 2H), 1.88 (d, 3H), 1.85-1.78 (m, 2H).

MS (ESI, Q$^+$) m/z 491, 493 (M+1 for $^{35}$Br and $^{37}$Br).

EXAMPLE 23

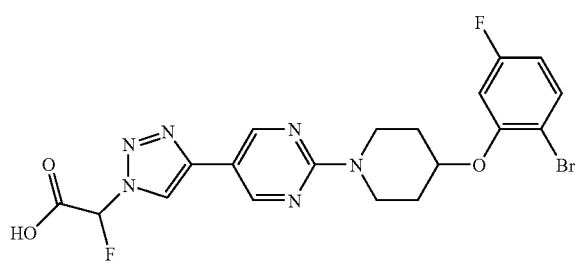

2-(4-{2-[4-(2-Bromo-5-fluorophenoxy)piperidin-1-yl]pyrimidin-5-yl}-1H-1,2,3-triazol-1-yl)(fluoro)acetic acid The title compound was prepared in a similar manner as that described for Example 22, using ethyl bromofluoroacetate in the place of ethyl 2-bromopropionate in step 1. The title compound was obtained as a yellow oil.

$^1$H NMR (400 MHz, acetone-d$_6$): δ 8.89 (s, 2H), 8.64 (s, 1H), 7.60 (dd, 1H), 7.11 (dd, 1H), 7.10 (d, 1H), 6.75-6.71 (m, 1H), 4.95-4.88 (m, 1H), 4.19-4.10 (m, 2H), 4.01-3.95 (m, 2H), 2.11-2.04 (m, 2H), 1.90-1.82 (m, 2H).

MS (ESI, Q$^+$) m/z 495, 497 (M+1 for $^{35}$Br and $^{37}$Br).

EXAMPLE OF A PHARMACEUTICAL FORMULATION

As a specific embodiment of an oral pharmaceutical composition of the present invention, a 100 mg potency tablet is composed of 100 mg of any one of the Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for a particular condition. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:
1. A compound of structural formula I:

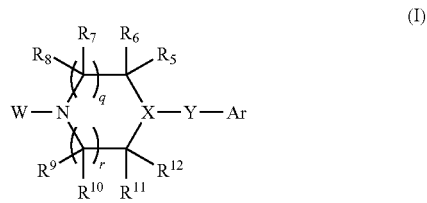

or a pharmaceutically acceptable salt thereof; wherein
each m is independently an integer from 0 to 4;
each n is independently an integer from 0 to 2;
each s is independently an integer from 1 to 3;
each t is independently an integer from 1 to 3;
q is 0 or 1;
r is 0 or 1;
Z is O, S, or NR$^4$;
X—Y is N—CR$^a$R$^b$, CR$^{14}$—S(O)$_{0-2}$, or CR$^{13}$—$^{CRa}$R$^b$;
W is heteroaryl selected from the group consisting of:

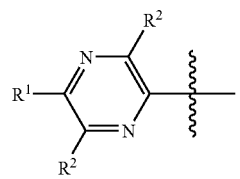

Ar is phenyl, naphthyl, or heteroaryl optionally substituted with one to five R$^3$ substituents;
R$^a$ and R$^b$ are each independently hydrogen or C$_{1-3}$ alkyl, wherein alkyl is optionally substituted with one to three substituents independently selected from fluorine and hydroxy;
R$^1$ is heteroaryl selected from the group consisting of:

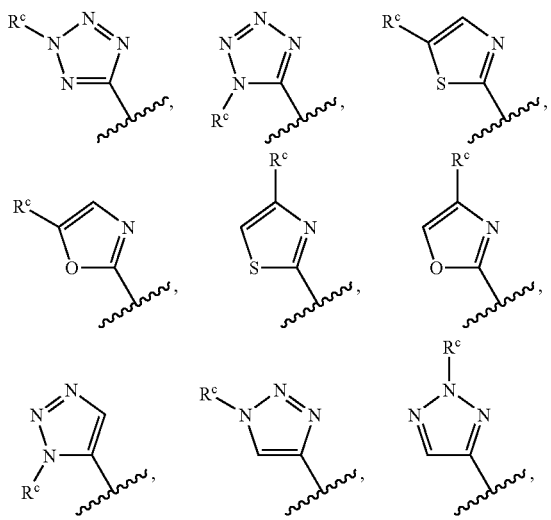

-continued

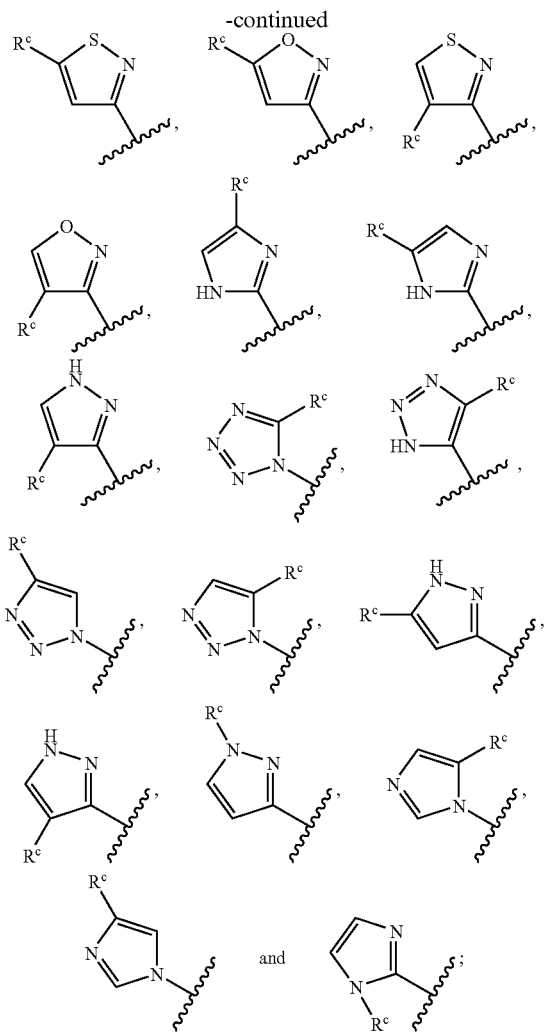

wherein $R^c$ is —$(CH_2)_mCO_2H$, —$(CH_2)_mCO_2C_{1-3}$ alkyl, —$(CH_2)_m$-Z-$(CH_2)_pCO_2H$, or —$(CH_2)_m$-Z-$(CH_2)_pCO_2C_{1-3}$ alkyl, wherein each ($CH_2$) methylene group is optionally substituted with one or two substituents selected from the group consisting of $C_{1-4}$ alkyl, fluorine, oxo, and hydroxy; and wherein said $R^1$ heteroaryl ring is optionally substituted with one substituent independently selected from the group consisting of cyano, halogen, $C_{1-4}$ alkyl, $C_{1-4}$ alkoxy, $C_{1-4}$ alkylthio, $C_{1-4}$ alkylsulfonyl, and trifluoromethyl;

each $R^2$ is independently selected from the group consisting of:
hydrogen,
halogen,
hydroxy,
cyano,
amino,
nitro,
$C_{1-4}$ alkyl, optionally substituted with one to five fluorines,
$C_{1-4}$ alkoxy, optionally substituted with one to five fluorines,
$C_{1-4}$ alkylthio, optionally substituted with one to five fluorines,
$C_{1-4}$ alkylsulfonyl,
carboxy,
$C_{1-4}$ alkyloxycarbonyl, and
$C_{1-4}$ alkylcarbonyl;

each $R^3$ is independently selected from the group consisting of:
$C_{1-6}$ alkyl,
$C_{2-6}$ alkenyl,
$(CH_2)_n$-phenyl,
$(CH_2)_n$-naphthyl,
$(CH_2)_n$-heteroaryl,
$(CH_2)_n$-heterocyclyl,
$(CH_2)_nC_{3-7}$ cycloalkyl,
halogen,
nitro,
$(CH_2)_nOR^4$,
$(CH_2)_nN(R^4)_2$,
$(CH_2)_nC\equiv N$,
$(CH_2)_nCO_2R^4$,
$(CH_2)_nNR^4SO_2R^4$,
$(CH_2)_nSO_2N(R^4)_2$,
$(CH_2)_nS(O)_{0-2}R^4$,
$(CH_2)_nNR^4C(O)N(R^4)_2$,
$(CH_2)_nC(O)N(R^4)_2$,
$(CH_2)_nNR^4C(O)R^4$,
$(CH_2)_nNR^4CO_2R^4$,
$(CH_2)_nC(O)R^4$,
$O(CH_2)_nC(O)N(R^4)_2$,
$(CH_2)_s$-Z-$(CH_2)_t$-phenyl,
$(CH_2)_s$-Z-$(CH_2)_t$-naphthyl,
$(CH_2)_s$-Z-$(CH_2)_t$-heteroaryl,
$(CH_2)_s$-Z-$(CH_2)_t$-heterocyclyl,
$(CH_2)_s$-Z-$(CH_2)_t$—$C_{3-7}$ cycloalkyl,
$(CH_2)_s$-Z-$(CH_2)_t$—$OR^4$,
$(CH_2)_s$-Z-$(CH_2)_t$—$N(R^4)_2$,
$(CH_2)_s$-Z-$(CH_2)_t$—$NR^4SO_2R^4$,
$(CH_2)_s$-Z-$(CH_2)_t$—$C\equiv N$,
$(CH_2)_s$-Z-$(CH_2)_t$—$CO_2R^4$,
$(CH_2)_s$-Z-$(CH_2)_t$—$SO_2N(R^4)_2$,
$(CH_2)_s$-Z-$(CH_2)_t$—$S(O)_{0-2}R^4$,
$(CH_2)_s$-Z-$(CH_2)_t$—$NR^4C(O)N(R^4)_2$,
$(CH_2)_s$-Z-$(CH_2)_t$—$C(O)N(R^4)_2$,
$(CH_2)_s$-Z-$(CH_2)_t$—$NR^4C(O)R^4$,
$(CH_2)_s$-Z-$(CH_2)_t$—$NR^4CO_2R^4$,
$(CH_2)_s$-Z-$(CH_2)_t$—$C(O)R^4$,
$CF_3$,
$CH_2CF_3$,
$OCF_3$, and
$OCH_2CF_3$;

in which phenyl, naphthyl, heteroaryl, cycloalkyl, and heterocyclyl are optionally substituted with one to three substituents independently selected from halogen, hydroxy, $C_{1-4}$ alkyl, trifluoromethyl, and $C_{1-4}$ alkoxy; and wherein any methylene ($CH_2$) carbon atom in $R^3$ is optionally substituted with one to two groups independently selected from fluorine, hydroxy, and $C_{1-4}$ alkyl; or two substituents when on the same methylene ($CH_2$) group are taken together with the carbon atom to which they are attached to form a cyclopropyl group;

each $R^4$ is independently selected from the group consisting of
hydrogen,
$C_{1-6}$ alkyl,
$(CH_2)_n$-phenyl,
$(CH_2)_n$-heteroaryl,
$(CH_2)_n$-naphthyl, and
$(CH_2)_nC_{3-7}$ cycloalkyl;

wherein alkyl, phenyl, heteroaryl, and cycloalkyl are optionally substituted with one to three groups independently selected from halogen, trifluoromethyl, $C_{1-4}$ alkyl, and $C_{1-4}$ alkoxy; or two $R^4$ groups together with the atom to which they are attached form a 4- to 8-membered mono- or bicyclic ring system optionally containing an additional heteroatom selected from O, S, NH, and $NC_{1-4}$ alkyl;

$R^5$, $R^6$, $R^7$, $R^8$, $R^9$, $R^{10}$, $R^{11}$, and $R^{12}$ are each independently hydrogen, fluorine, or $C_{1-3}$ alkyl, wherein alkyl is optionally substituted with one to three substituents independently selected from fluorine and hydroxy;

$R^{13}$ is hydrogen, $C_{1-3}$ alkyl, fluorine, or hydroxy; and each $R^{14}$ is hydrogen or $C_{1-3}$ alkyl.

2. The compound of claim 1 wherein m is 1 or 2.

3. The compound of claim 1 wherein q and r are both 1.

4. The compound of claim 1 wherein X—Y is CH—O.

5. The compound of claim 4 wherein Ar is phenyl substituted with one to three $R^3$ substituents.

6. The compound of claim 1 wherein $R^5$, $R^6$, $R^7$, $R^8$, $R^9$, $R^{10}$, $R^{11}$, and $R^{12}$ are each hydrogen.

7. The compound of claim 1 wherein each $R^2$ is hydrogen.

8. The compound of claim 1 wherein $R^1$ is heteroaryl selected from the group consisting of

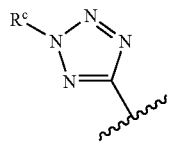 and 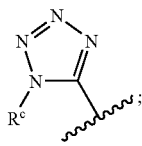;

wherein $R^c$ is —$CH_2CO_2H$ or —$CH_2CO_2C_{1-3}$ alkyl.

9. The compound of claim 8 wherein $R^1$ is

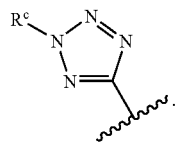.

10. The compound of claim 1 wherein q and r are both 1; X—Y is CH—O; W is:

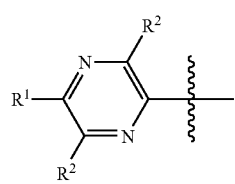

and $R^1$ is heteroaryl selected from the group consisting of:

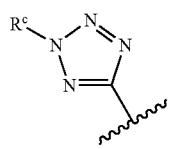 and 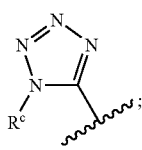;

wherein $R^c$ is —$CH_2CO_2H$ or —$CH_2CO_2C_{1-3}$ alkyl.

11. The compound of claim 10 wherein W is

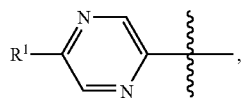, and $R^5$, $R^6$, $R^7$, $R^8$, $R^9$, $R^{10}$, $R^{11}$, and $R^{12}$ are each hydrogen.

12. A compound which is

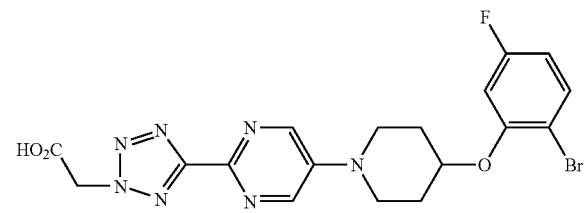

or a pharmaceutically acceptable salt thereof.

13. A pharmaceutical composition comprising a compound in accordance with claim 1 in combination with a pharmaceutically acceptable carrier.

14. A compound which is

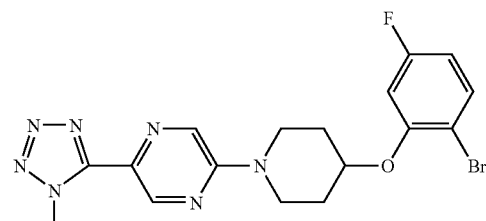

or a pharmaceutically acceptable salt thereof.

15. A compound which is

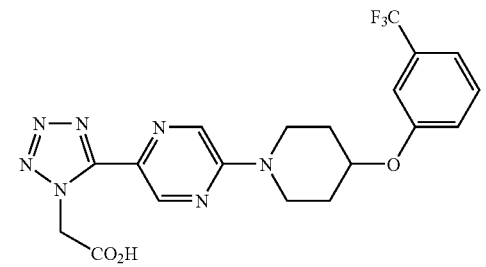

or a pharmaceutically acceptable salt thereof.

16. A compound which is

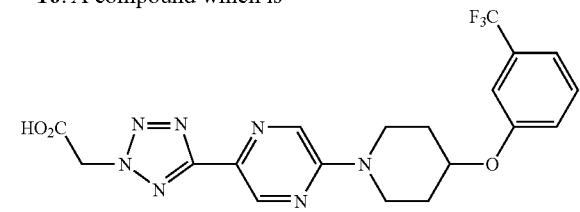

or a pharmaceutically acceptable salt thereof.

17. A method for treating diabetes in a mammal in need thereof comprising administering to said mammal a therapeutically effective amount of a compound of claim 1.

18. A method for treating Type 2 diabetes in a mammal in need thereof comprising administering to said mammal a therapeutically effective amount of a compound of claim 1.

19. A method for treating obesity in a mammal in need thereof comprising administering to said mammal a therapeutically effective amount of a compound of claim 1.

* * * * *

UNITED STATES PATENT AND TRADEMARK OFFICE
CERTIFICATE OF CORRECTION

PATENT NO.        : 7,582,633 B2
APPLICATION NO.   : 12/011309
DATED             : September 1, 2009
INVENTOR(S)       : Yves Leblanc et al.

It is certified that error appears in the above-identified patent and that said Letters Patent is hereby corrected as shown below:

IN THE CLAIMS:

Claim 1, Line 26, Cancel "$CR^{13-CR^aR^b}$" and substitute therefor -- $CR^{13}-CR^aR^b$ --.

Signed and Sealed this

Twenty-seventh Day of October, 2009

David J. Kappos
*Director of the United States Patent and Trademark Office*

UNITED STATES PATENT AND TRADEMARK OFFICE
CERTIFICATE OF CORRECTION

PATENT NO. : 7,582,633 B2
APPLICATION NO. : 12/011309
DATED : September 1, 2009
INVENTOR(S) : Yves Leblanc et al.

It is certified that error appears in the above-identified patent and that said Letters Patent is hereby corrected as shown below:

IN THE CLAIMS:

Column 54, Claim 1, Line 26, Cancel "$CR^{13-CR^aR^b}$" and substitute therefor -- $CR^{13}-CR^aR^b$ --.

This certificate supersedes the Certificate of Correction issued October 27, 2009.

Signed and Sealed this

Seventeenth Day of November, 2009

David J. Kappos
*Director of the United States Patent and Trademark Office*

UNITED STATES PATENT AND TRADEMARK OFFICE
CERTIFICATE OF CORRECTION

PATENT NO.        : 7,582,633 B2
APPLICATION NO.  : 12/011309
DATED            : September 1, 2009
INVENTOR(S)      : Yves Leblanc et al.

Page 1 of 1

It is certified that error appears in the above-identified patent and that said Letters Patent is hereby corrected as shown below:

IN THE CLAIMS:

Column 58 Claim 12, Lines 11-21, Cancel

"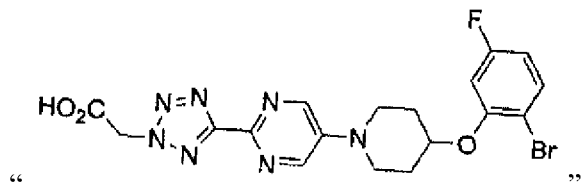"

and substitute therefor

--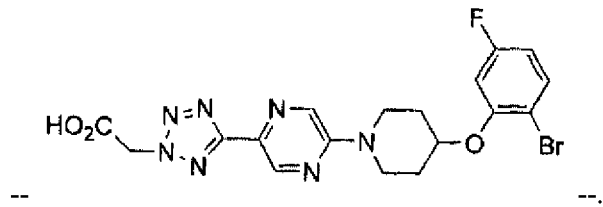--.

Signed and Sealed this

Twenty-ninth Day of December, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,582,633 B2 | Page 1 of 1 |
| APPLICATION NO. | : 12/011309 | |
| DATED | : September 1, 2009 | |
| INVENTOR(S) | : Yves Leblanc et al. | |

It is certified that error appears in the above-identified patent and that said Letters Patent is hereby corrected as shown below:

IN THE CLAIMS:

Claim 1 at Column 54, Line 26, insert --$CR^{14}$-O,-- after N-$CR^aR^b$, but before $CR^{14}$-$S(O)_{0-2}$.

Signed and Sealed this
Fifth Day of July, 2011

David J. Kappos
*Director of the United States Patent and Trademark Office*